US005652340A

United States Patent [19]
Kohwi-Shigematsu et al.

[11] Patent Number: 5,652,340
[45] Date of Patent: Jul. 29, 1997

[54] MATRIX-ASSOCIATING DNA-BINDING PROTEIN, NUCLEIC ACIDS ENCODING THE SAME AND METHODS FOR DETECTING THE NUCLEIC ACIDS

[75] Inventors: Terumi Kohwi-Shigematsu; Yoshinori Kohwi; Liliane A. Dickinson, all of San Diego, Calif.

[73] Assignee: La Jolla Cancer Research Foundation, La Jolla, Calif.

[21] Appl. No.: 473,122

[22] Filed: Jun. 6, 1995

Related U.S. Application Data

[63] Continuation of Ser. No. 934,034, Aug. 21, 1992, abandoned.
[51] Int. Cl.$^6$ .................................................. A61K 38/17
[52] U.S. Cl. ............................................................. 530/358
[58] Field of Search ............................................. 530/358

[56] References Cited

PUBLICATIONS

Tizard, *Immunology: An Introduction*, Saunders College Publishing, Philadelphia, 1988, pp. 141–146.

Nakagomi et al. A novel DNA–binding motif in the nuclear matrix attachment DNA–binding protein SATB1. Molecular and Cellular Biology. vol. 14, No. 3, pp. 1852–1860. Mar. 1994.

Solomon, Mark J., et al., "A Mammalian High Mobility Group Protein Recognizes any Stretch of Six A–T Base Pairs in Duplex DNA", Proc. Natl. Acad. Sci. USA. 83:1276–1280 (1986).

Umek, Robert M. and Kowalski, David, "The Ease of DNA Unwinding as a Determinant of Initiation at Yeast Replication Origins". Cell. 52:559–567 (1988).

Mielke, Christian et al., "Hierarchical Binding of DNA Fragments Derived From Scaffold–Attached Regions: Correlation of Properties in Vitro and Function in Vivo". Biochem. 29:7475–7485 (1990).

Kohwi–Shigematsu, Terumi and Kohwi, yoshinori, "Torsional Street Stabilized Extended Base Unpairing in Suppressor Sites Flanking Immunoglobulin Heavy Chain Enhancer". Biochem. 29:9551–9560 (1990).

Phi-Van, Loc et al., "The Chicken Lysozyme 5' Matrix Attachment Region Increases Transcription From a Heterologous Promoter in Heterologous Cells and Dampens Position Effects on the Expression of Transfected Genes". Mole. and Cell. Biol. 10:2302–2307 (1990).

von Kries, Jens P. et al., "A Matrix/Scaffold Attachment Region Binding Protein: Identification, Purification, and Mode of Binding". Cell. 64:123–135 (1991).

Klehr, Dagmar et al., "Scaffold–Attached Regions from the Human Interferon β Domain Can Be Used To Enhance the Stable Expression of Genes under the Control of Various Promoters". Biochem. 30:1264–1270 (1991).

Brotherton, Timothy et al., "Avian Nuclear Matrix Proteins Bind Very Tightly to Cellular DNA of the β–Glovin Gene Enhancer in a Tissue–Specific Fashion". Biochem. 30:5845–5850 (1991).

Bode, J. et al., "Biological Significance of Unwinding Capability of Nuclear Matrix–Associating DNAs". Science. 255:195–197 (1992).

Romig, Helmut et al. "Characterization of SAF–A, a Novel Nuclear DNA Binding Protein from HeLa Cells with High Affinity for Nuclear Matrix/Scaffold Attachment DNA Elements." Embo J. 11:3431–3440 (1992).

Dickinson, Liliane A. et al. "A Tissue–Specific MAR/SAR DNA–Binding Protein with Unusual Binding Site Recognition." Cell. 70:631–645 (1992).

*Primary Examiner*—Keith D. Hendricks
*Assistant Examiner*—Brian Lathrop
*Attorney, Agent, or Firm*—Campbell & Flores

[57] ABSTRACT

The present invention provides a novel human protein, SATB1, that binds matrix/scaffold-associating DNA regions (MARs). The novel human protein, predominantly expressed in the thymus, has an approximate molecular weight of about 85.9 kD. The SATB1 cDNA encodes a 763 amino acid sequence protein that is capable of binding to special AT rich sequences (ATC sequences). The invention further provides antibodies specifically reactive with such protein. Isolated nucleic acids encoding the novel MAR-binding protein are also provided, as well as vectors containing the nucleic acids and recombinant host cells transformed with such vectors. The invention further provides methods of detecting such nucleic acids by contacting a sample with a nucleic acid probe having a nucleotide sequence capable of hybridizing with the isolated nucleic acids of the present invention. Such probes can correspond to the ATC sequences.

2 Claims, 14 Drawing Sheets

FIG. 4B

XbaI 5'-TTCTCTTTAA...TTAATATATTAGAA-3' HindIII
    3'-AAGAGAAATT...AATTATATAATCTT-5'

5' REGION

```
                            Site I
                              83
                              |
aaaggaacacAGAAGTATGTGTATGGAATATTAGAAGATGTTGcttttactct
tttccttgtgTCTTCATACACATACCTTATAATCTTCTACAACgaaaatgaga
         51
         |
```

```
                Site II                    Site III
                 305                           332
                  |                             |
tccagaactgACTTTTAACAATAATAAATTAAGTTTAAAATATTTTAAATGAATTGAGcaatgttgag
aggtcttgacTGAAAATTGTTATTATTTAATTCAAATTTTATAAAATTTACTTAACTCgttacaactc
         284
         |
```

3' REGION

```
                Site IV                          Site V
                 753
                  |
ggactttagtgTCTTTAATTTCTAATATATATTAGAAAACTTCTTAAAATTACTCTATTATTCTTCTCC
cctgaaatcacAGAAATTAAAGATTATATAATCTTTTGAAGAATTTTAATGAGATAATAAGAAGAAGG
         732
         |
```

```
             Site VI
              800
              |
CTCTGATTATTGGTctccatt
GAGACTAATAACCAgagggtaa
         790
         |
```

FIG. 6A

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 2946 base pairs
        ( B ) TYPE: nucleic acid
        ( C ) STRANDEDNESS: unknown
        ( D ) TOPOLOGY: linear ( i i ) MOLECULE TYPE: cDNA ( x i ) SEQUENCE DESCRIPTION: SEQ ID NO:1:

```
GGGGGGAAAG  GAAAATAATA  CAATTTCAGG  GGAAGTCGCC  TTCAGGTCTG  CTGCTTTTTT      60

ATTTTTTTTT  TTTAATTAA   AAAAAAAAG   GACATAGAAA  ACATCAGTCT  TGAACTTCTC     120

TTCAAGAACC  CGGGCTGCAA  AGGAAATCTC  CTTTGTTTTT  GTTATTTATG  TGCTGTCAAG     180

TTTTGAAGTG  GTGATCTTTA  GACAGTGACT  GAGTATGGAT  CATTTGAACG  AGGCAACTCA     240

GGGGAAAGAA  CATTCAGAAA  TGTCTAACAA  TGTGAGTGAT  CCGAAGGGTC  CACCAGCCAA     300

GATTGCCCGC  CTGGAGCAGA  ACGGGAGCCC  GCTAGGAAGA  GGAAGGCTTG  GGAGTACAGG     360

TGCAAAAATG  CAGGGAGTGC  CTTTAAAACA  CTCGGGCCAT  CTGATGAAAA  CCAACCTTAG     420

GAAAGGAACC  ATGCTGCCAG  TTTTCTGTGT  GGTGGAACAT  TATGAAAACG  CCATTGAATA     480

TGATTGCAAG  GAGGAGCATG  CAGAATTTGT  GCTGGTGAGA  AAGGATATGC  TTTTCAACCA     540

GCTGATCGAA  ATGGCATTGC  TGTCTCTAGG  TTATTCACAT  AGCTCTGCTG  CCCAGGCCAA     600

AGGGCTAATC  CAGGTTGGAA  AGTGGAATCC  AGTTCCACTG  TCTTACGTGA  CAGATGCCCC     660

TGATGCTACA  GTAGCAGATA  TGCTTCAAGA  TGTGTATCAT  GTGGTCACAT  TGAAAATTCA     720

GTTACACAGT  TGCCCCAAAC  TAGAAGACTT  GCCTCCCGAA  CAATGGTCGC  ACACCACAGT     780
```

-continued

| | | | | | | |
|---|---|---|---|---|---|---|
| GAGGAATGCT | CTGAAGGACT | TACTGAAAGA | TATGAATCAG | AGTTCATTGG | CCAAGGAGTG | 840 |
| CCCCCTTTCA | CAGAGTATGA | TTTCTTCCAT | TGTGAACAGT | ACTTACTATG | CAAATGTCTC | 900 |
| AGCAGCAAAA | TGTCAAGAAT | TTGGAAGGTG | GTACAAACAT | TCAAGAAGA | CAAAAGATAT | 960 |
| GATGGTTGAA | ATGGATAGTC | TTTCTGAGCT | ATCCAGCAA | GGCGCCAATC | ATGTCAATTT | 1020 |
| TGGCCAGCAA | CCAGTTCCAG | GGAACACAGC | CGAGCAGCCT | CCATCCCTG | CGCAGCTCTC | 1080 |
| CCATGGCAGC | CAGCCCTCTG | TCCGGACACC | TCTTCCAAAC | CTGCACCCTG | GGCTCGTATC | 1140 |
| AACACCTATC | AGTCCTCAAT | TGGTCAACCA | GCAGCTGGTG | ATGGCTCAGC | TGCTGAACCA | 1200 |
| GCAGTATGCA | GTGAATAGAC | TTTTAGCCCA | GCAGTCCTTA | AACCAACAAT | ACTTGAACCA | 1260 |
| CCCTCCCCCT | GTCAGTAGAT | CTATGAATAA | GCCTTTGGAG | CAACAGGTTT | CGACCAACAC | 1320 |
| AGAGGTGTCT | TCCGAAATCT | ACCAGTGGGT | ACGCGATGAA | CTGAAACGAG | CAGGAATCTC | 1380 |
| CCAGGCGGTA | TTTGCACGTG | TGGCTTTTAA | CAGAACTCAG | GGCTTGCTTT | CAGAAATCCT | 1440 |
| CCGAAAGGAA | GAGGACCCCA | AGACTGCATC | CCAGTCTTTG | CTGGTAAACC | TTCGGGCTAT | 1500 |
| GCAGAATTTC | TTGCAGTTAC | CGGAAGCTGA | AAGAGACCGA | ATATACCAGG | ACGAAAGGGA | 1560 |
| AAGGAGCTTG | AATGCTGCCT | CGGCCATGGG | TCCTGCCCCC | CTCATCAGCA | CACCACCCAG | 1620 |
| CCGTCCTCCC | CAGGTGAAAA | CAGCTACTAT | TGCCACTGAA | AGGAATGGGA | AACCAGAGAA | 1680 |
| CAATACCATG | AACATTAATG | CTTCCATTTA | TGATGAGATT | CAGCAGGAAA | TGAAGCGTGC | 1740 |
| TAAAGTGTCT | CAAGCACTGT | TTGCAAAGGT | TGCAGCAACC | AAAAGCCAGG | GATGGTTGTG | 1800 |
| CGAGCTGTTA | CGCTGGAAAG | AAGATCCTTC | TCCAGAAAAC | AGAACCCTGT | GGGAGAACCT | 1860 |
| CTCCATGATC | CGAAGGTTCC | TCAGTCTTCC | TCAGCCAGAA | CGTGATGCCA | TTTATGAACA | 1920 |
| GGAGAGCAAC | GCGGTGCATC | ACCATGGCGA | CAGGCCGCCC | CACATTATCC | ATGTTCCAGC | 1980 |
| AGAGCAGATT | CAGCAACAGC | AGCAGCAACA | GCAACAGCAG | CAGCAGCAGC | AGCAGGCACC | 2040 |
| GCCGCCTCCA | CAGCCACAGC | AGCAGCCACA | GACAGGCCCT | CGGCTCCCCC | CACGGCAACC | 2100 |
| CACGGTGGCC | TCTCCAGCAG | AGTCAGATGA | GGAAAACCGA | CAGAAGACCC | GGCCACGAAC | 2160 |
| AAAAATTTCA | GTGGAAGCCT | TGGGAATCCT | CCAGAGTTTC | ATACAAGACG | TGGGCCTGTA | 2220 |
| CCCTGACGAA | GAGGCCATCC | AGACTCTGTC | TGCCCAGCTC | GACCTTCCCA | AGTACACCAT | 2280 |
| CATCAAGTTC | TTTCAGAACC | AGCGGTACTA | TCTCAAGCAC | CACGGCAAAC | TGAAGGACAA | 2340 |
| TTCCGGTTTA | GAGGTCGATG | TGGCAGAATA | TAAAGAAGAG | GAGCTGCTGA | AGGATTTGGA | 2400 |
| AGAGAGTGTC | CAAGATAAAA | ATACTAACAC | CCTTTTTTCA | GTGAAACTAG | AAGAAGAGCT | 2460 |
| GTCAGTGGAA | GGAAACACAG | ACATTAATAC | TGATTTGAAA | GACTGAGATA | AAGTATTTG | 2520 |
| TTTCGTTCAA | CAGTGCCACT | GGTATTTACT | AACAAAATGA | AAGTCCACC | TTGTCTTCTC | 2580 |
| TCAGAAAACC | TTTGTTGTTC | ATTGTTTGGC | CAATGAATCT | TCAAAAACTT | GCACAAACAG | 2640 |
| AAAAGTTGGA | AAAGGATAAT | ACAGACTGCA | CTAAATGTTT | TCCTCTGTTT | TACAAACTGC | 2700 |
| TTGGCAGCCC | CAGGTGAAGC | ATCAAGGATT | GTTTGGTATT | AAAATTTGTG | TTCACGGGAT | 2760 |
| GCACCAAAGT | GTGTACCCCG | TAAGCATGAA | ACCAGTGTTT | TTTGTTTTTT | TTTAGTTCT | 2820 |
| TATTCCGGAG | CCTCAAACAA | GCATTATACC | TTCTGTGATT | ATGATTTCCT | CTCCTATAAT | 2880 |
| TATTTCTGTA | GCACTCCACA | CTGATCTTTG | GAAACTTGCC | CCTTATTTAA | AAAAAAAAA | 2940 |
| AAAAAA | | | | | | 2946 |

( 2 ) INFORMATION FOR SEQ ID NO:2:

( i ) SEQUENCE CHARACTERISTICS:
        ( A ) LENGTH: 763 amino acids
        ( B ) TYPE: amino acid 5,652,340

-continued (C) STRANDEDNESS: single
(D) TOPOLOGY: linear (ii) MOLECULE TYPE: protein (xi) SEQUENCE DESCRIPTION: SEQ ID NO:2:

| Met | Asp | His | Leu | Asn | Glu | Ala | Thr | Gln | Gly | Lys | Glu | His | Ser | Glu | Met |
|---|---|---|---|---|---|---|---|---|---|---|---|---|---|---|---|
| 1 | | | | 5 | | | | | 10 | | | | | 15 | |
| Ser | Asn | Asn | Val | Ser | Asp | Pro | Lys | Gly | Pro | Pro | Ala | Lys | Ile | Ala | Arg |
| | | | 20 | | | | 25 | | | | | 30 | | | |
| Leu | Glu | Gln | Asn | Gly | Ser | Pro | Leu | Gly | Arg | Gly | Arg | Leu | Gly | Ser | Thr |
| | | 35 | | | | | 40 | | | | | 45 | | | |
| Gly | Ala | Lys | Met | Gln | Gly | Val | Pro | Leu | Lys | His | Ser | Gly | His | Leu | Met |
| | 50 | | | | 55 | | | | | | 60 | | | | |
| Lys | Thr | Asn | Leu | Arg | Lys | Gly | Thr | Met | Leu | Pro | Val | Phe | Cys | Val | Val |
| 65 | | | | 70 | | | | | 75 | | | | | | 80 |
| Glu | His | Tyr | Glu | Asn | Ala | Ile | Glu | Tyr | Asp | Cys | Lys | Glu | Glu | His | Ala |
| | | | | 85 | | | | | 90 | | | | | 95 | |
| Glu | Phe | Val | Leu | Val | Arg | Lys | Asp | Met | Leu | Phe | Asn | Gln | Leu | Ile | Glu |
| | | | | 100 | | | | | 105 | | | | | 110 | |
| Met | Ala | Leu | Leu | Ser | Leu | Gly | Tyr | Ser | His | Ser | Ser | Ala | Ala | Gln | Ala |
| | | | 115 | | | | | 120 | | | | | 125 | | |
| Lys | Gly | Leu | Ile | Gln | Val | Gly | Lys | Trp | Asn | Pro | Val | Pro | Leu | Ser | Tyr |
| | 130 | | | | | 135 | | | | | 140 | | | | |
| Val | Thr | Asp | Ala | Pro | Asp | Ala | Thr | Val | Ala | Asp | Met | Leu | Gln | Asp | Val |
| 145 | | | | | 150 | | | | | 155 | | | | | 160 |
| Tyr | His | Val | Val | Thr | Leu | Lys | Ile | Gln | Leu | His | Ser | Cys | Pro | Lys | Leu |
| | | | | 165 | | | | | 170 | | | | | 175 | |
| Glu | Asp | Leu | Pro | Pro | Glu | Gln | Trp | Ser | His | Thr | Thr | Val | Arg | Asn | Ala |
| | | | 180 | | | | | 185 | | | | | 190 | | |
| Leu | Lys | Asp | Leu | Leu | Lys | Asp | Met | Asn | Gln | Ser | Ser | Leu | Ala | Lys | Glu |
| | | 195 | | | | | 200 | | | | | 205 | | | |
| Cys | Pro | Leu | Ser | Gln | Ser | Met | Ile | Ser | Ser | Ile | Val | Asn | Ser | Thr | Tyr |
| | 210 | | | | | 215 | | | | | 220 | | | | |
| Tyr | Ala | Asn | Val | Ser | Ala | Ala | Lys | Cys | Gln | Glu | Phe | Gly | Arg | Trp | Tyr |
| 225 | | | | | 230 | | | | | 235 | | | | | 240 |
| Lys | His | Phe | Lys | Lys | Thr | Lys | Asp | Met | Met | Val | Glu | Met | Asp | Ser | Leu |
| | | | | 245 | | | | | 250 | | | | | 255 | |
| Ser | Glu | Leu | Ser | Gln | Gln | Gly | Ala | Asn | His | Val | Asn | Phe | Gly | Gln | Gln |
| | | | 260 | | | | | 265 | | | | | 270 | | |
| Pro | Val | Pro | Gly | Asn | Thr | Ala | Glu | Gln | Pro | Pro | Ser | Pro | Ala | Gln | Leu |
| | | 275 | | | | | 280 | | | | | 285 | | | |
| Ser | His | Gly | Ser | Gln | Pro | Ser | Val | Arg | Thr | Pro | Leu | Pro | Asn | Leu | His |
| | 290 | | | | | 295 | | | | | 300 | | | | |
| Pro | Gly | Leu | Val | Ser | Thr | Pro | Ile | Ser | Pro | Gln | Leu | Val | Asn | Gln | Gln |
| 305 | | | | | 310 | | | | | 315 | | | | | 320 |
| Leu | Val | Met | Ala | Gln | Leu | Leu | Asn | Gln | Gln | Tyr | Ala | Val | Asn | Arg | Leu |
| | | | | 325 | | | | | 330 | | | | | 335 | |
| Leu | Ala | Gln | Gln | Ser | Leu | Asn | Gln | Gln | Tyr | Leu | Asn | His | Pro | Pro | Pro |
| | | | 340 | | | | | 345 | | | | | 350 | | |
| Val | Ser | Arg | Ser | Met | Asn | Lys | Pro | Leu | Glu | Gln | Gln | Val | Ser | Thr | Asn |
| | | 355 | | | | | 360 | | | | | 365 | | | |
| Thr | Glu | Val | Ser | Ser | Glu | Ile | Tyr | Gln | Trp | Val | Arg | Asp | Glu | Leu | Lys |
| | 370 | | | | | 375 | | | | | 380 | | | | |
| Arg | Ala | Gly | Ile | Ser | Gln | Ala | Val | Phe | Ala | Arg | Val | Ala | Phe | Asn | Arg |

|     |     |     |     |     |     |     |     |     |     |     |     |     |     |     |
| --- | --- | --- | --- | --- | --- | --- | --- | --- | --- | --- | --- | --- | --- | --- |
| 385 |  |  |  |  | 390 |  |  |  | 395 |  |  |  |  | 400 |
| Thr | Gln | Gly | Leu | Leu<br>405 | Ser | Glu | Ile | Leu | Arg<br>410 | Lys | Glu | Glu | Asp | Pro<br>415 | Lys |
| Thr | Ala | Ser | Gln<br>420 | Ser | Leu | Leu | Val | Asn<br>425 | Leu | Arg | Ala | Met | Gln<br>430 | Asn | Phe |
| Leu | Gln | Leu<br>435 | Pro | Glu | Ala | Glu | Arg<br>440 | Asp | Arg | Ile | Tyr | Gln<br>445 | Asp | Glu | Arg |
| Glu | Arg<br>450 | Ser | Leu | Asn | Ala | Ala<br>455 | Ser | Ala | Met | Gly | Pro<br>460 | Ala | Pro | Leu | Ile |
| Ser<br>465 | Thr | Pro | Pro | Ser | Arg<br>470 | Pro | Pro | Gln | Val | Lys<br>475 | Thr | Ala | Thr | Ile | Ala<br>480 |
| Thr | Glu | Arg | Asn | Gly<br>485 | Lys | Pro | Glu | Asn | Asn<br>490 | Thr | Met | Asn | Ile | Asn<br>495 | Ala |
| Ser | Ile | Tyr | Asp<br>500 | Glu | Ile | Gln | Gln | Glu<br>505 | Met | Lys | Arg | Ala | Lys<br>510 | Val | Ser |
| Gln | Ala | Leu<br>515 | Phe | Ala | Lys | Val | Ala<br>520 | Ala | Thr | Lys | Ser | Gln<br>525 | Gly | Trp | Leu |
| Cys | Glu<br>530 | Leu | Leu | Arg | Trp | Lys<br>535 | Glu | Asp | Pro | Ser | Pro<br>540 | Glu | Asn | Arg | Thr |
| Leu<br>545 | Trp | Glu | Asn | Leu | Ser<br>550 | Met | Ile | Arg | Arg | Phe<br>555 | Leu | Ser | Leu | Pro | Gln<br>560 |
| Pro | Glu | Arg | Asp | Ala<br>565 | Ile | Tyr | Glu | Gln | Glu<br>570 | Ser | Asn | Ala | Val | His<br>575 | His |
| His | Gly | Asp | Arg<br>580 | Pro | Pro | His | Ile | Ile<br>585 | His | Val | Pro | Ala | Glu<br>590 | Gln | Ile |
| Gln | Gln | Gln | Gln | Gln<br>595 | Gln | Gln | Gln | Gln | Gln<br>600 | Gln | Gln | Gln | Gln | Gln<br>605 | Ala |
| Pro | Pro | Pro<br>610 | Pro | Gln | Pro | Gln | Gln<br>615 | Gln | Gln | Pro | Gln | Thr<br>620 | Gly | Pro | Arg | Leu |
| Pro<br>625 | Pro | Arg | Gln | Pro | Thr<br>630 | Val | Ala | Ser | Pro | Ala<br>635 | Glu | Ser | Asp | Glu<br>640 |
| Asn | Arg | Gln | Lys | Thr<br>645 | Arg | Pro | Arg | Thr | Lys<br>650 | Ile | Ser | Val | Glu | Ala<br>655 | Leu |
| Gly | Ile | Leu | Gln<br>660 | Ser | Phe | Ile | Gln | Asp<br>665 | Val | Gly | Leu | Tyr | Pro<br>670 | Asp | Glu |
| Glu | Ala | Ile<br>675 | Gln | Thr | Leu | Ser | Ala<br>680 | Gln | Leu | Asp | Leu | Pro<br>685 | Lys | Tyr | Thr |
| Ile | Ile<br>690 | Lys | Phe | Phe | Gln | Asn<br>695 | Gln | Arg | Tyr | Tyr | Leu<br>700 | Lys | His | His | Gly |
| Lys<br>705 | Leu | Lys | Asp | Asn | Ser<br>710 | Gly | Leu | Glu | Val | Asp<br>715 | Val | Ala | Glu | Tyr | Lys<br>720 |
| Glu | Glu | Glu | Leu | Leu<br>725 | Lys | Asp | Leu | Glu | Glu<br>730 | Ser | Val | Gln | Asp | Lys<br>735 | Asn |
| Thr | Asn | Thr | Leu<br>740 | Phe | Ser | Val | Lys | Leu<br>745 | Glu | Glu | Glu | Leu | Ser<br>750 | Val | Glu |
| Gly | Asn | Thr<br>755 | Gln | Ile | Asn | Thr | Asp<br>760 | Leu | Lys | Asp |  |  |  |  |  |

( 2 ) INFORMATION FOR SEQ ID NO:3:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CTTCTAATA  9

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

AATAATAAAT  10

( 2 ) INFORMATION FOR SEQ ID NO:5:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

ATATTTTT  8

( 2 ) INFORMATION FOR SEQ ID NO:6:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

TTCTAATATA T  11

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

AATAATAGAG TAATTTT  17

( 2 ) INFORMATION FOR SEQ ID NO:8:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

ACCAATAATC A  11

( 2 ) INFORMATION FOR SEQ ID NO:9:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

TCTTTAATTT CTAATATATT TAGAATTC     28

( 2 ) INFORMATION FOR SEQ ID NO:10:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

TTCTAAATAT ATTAGAAATT AAAGAGAA     28

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

TCTTTAATTT CTACTGCTTT AGAATTC     27

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

AAGATTTATA TAATCTTTAA TTTCT     25

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

AAGATTTCGT CATCTTTAAT TTCT     24

( 2 ) INFORMATION FOR SEQ ID NO:14:

( i ) SEQUENCE CHARACTERISTICS:

( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

TATATTAGAA A  11

( 2 ) INFORMATION FOR SEQ ID NO:15:

( i ) SEQUENCE CHARACTERISTICS:
        ( A ) LENGTH: 53 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:15:

AAAGGAACAC AGAAGTATGT GTATGGAATA TTAGAAGATG TTGCTTTTAC TCT  53

( 2 ) INFORMATION FOR SEQ ID NO:16:

( i ) SEQUENCE CHARACTERISTICS:
        ( A ) LENGTH: 69 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:16:

TCCAGAACTG ACTTTTAACA ATAATAAATT AAGTTTAAAA TATTTTAAA TGAATTGAGC  60

AATGTTGAG  69

( 2 ) INFORMATION FOR SEQ ID NO:17:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:17:

GGACTTTAGT GTCTTTAATT TCTAATATAT TTAGAAAACT TCTTAAAATT ACTCTATTAT  60

TCTTCTTCCC TCTGATTATT GGTCTCCATT  90

( 2 ) INFORMATION FOR SEQ ID NO:18:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:18:

AGAAGTATGT GTATGGAATA TTAGAAGATG TTG  33

( 2 ) INFORMATION FOR SEQ ID NO:19:

( i ) SEQUENCE CHARACTERISTICS:
        ( A ) LENGTH: 33 base pairs (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:19:

AGAACTATGT CTATGCAATA TTAGAAGATC TTG 33

MATRIX-ASSOCIATING DNA-BINDING PROTEIN, NUCLEIC ACIDS ENCODING THE SAME AND METHODS FOR DETECTING THE NUCLEIC ACIDS

This application is a continuation of application Ser. No. 07/934,034, filed Aug. 21, 1992 now abandoned.

This invention was made in part with Government support under Grant Nos. ROI CA39681 and ROI CA51377, an American Cancer Society Faculty Award, and funds provided by the Cigarette and Tobacco Surtax Fund of the State of California through the Tobacco-Related Disease Research Program of the University of California Grant No. IKT98. The Government may have certain rights in this invention.

BACKGROUND OF THE INVENTION

The present invention generally relates to a novel tissue-specific matrix- or scaffold-associating DNA region (MAR) binding protein. The invention additionally relates to the cloning of a human cDNA encoding the novel protein and antibodies specifically reactive with such protein.

Eukaryotic chromosomes are thought to be organized into a high order structure consisting of discrete and topologically independent loop domains, which would be fastened at their bases to the intranuclear framework by non-histone proteins as reviewed in Gasser and Laemmli, Trends Genet. 3:16–22 (1987). The loop organization of chromosomes may be important not only for compaction of the chromatin fiber, but also for the regulation of gene expression and replication. Each domain is believed to represent an independent unit of gene activity, which would be insulated from the regulatory mechanisms of neighboring domains and thus protected from chromosomal position effects.

The above model implies that specific DNA sequences exist at the bases of the DNA loops and proteins that bind to these sequences to separate one domain from another. Much effort has been devoted to identifying these sequences. A biochemical criterion used to define putative boundary sequences is their high binding affinity to the nuclear matrix or scaffold, which is defined as the residual structures left in the nucleus after removal of histones and other proteins. Specific DNA segments that strongly bind the nuclear matrix/scaffold have been identified in a number of different species including human, mouse, Drosophila, chicken, plant, and yeast as reviewed in Phi-Van and Stratling, Proc. Mol. Subcell. Biol. 11:1–11 (1990). These sequences are called MARs or SARs for matrix- or scaffold-associating regions (collectively referred to herein as MARs). Such MARs often contain or are located in close vicinity to regulatory sequences, including enhancer sequences.

Although some MARs are found in intragenic locations, most MARs are found at the boundaries of transcription units where they may delimit the ends of an active chromatin domain. Furthermore, A-elements of the chicken lysozyme gene, which contain DNA with high affinity to the nuclear matrix as described in Phi-Van and Stratling, EMBO J. 7:655–664 (1988), augment the transcriptional activity of a linked gene in a position-independent, copy number-dependent manner in stably transfected cells, suggesting that MARs can act as boundary sequences in vivo. The locus control region of the human β-globin domain, characterized by a set of tissue-specific DNase I hypersensitive sites, also contains MARs and confers copy number-dependent high levels of erythroid-specific expression to a linked gene. The specific role of MARs in either A-elements or locus control region activity remains unclear. Recently, specialized chromatin structures (scs and scs') which are MAR-like AT rich sequences, located at the boundaries of a Drosophila heat-shock gene, were shown to insulate the regulatory influence of adjacent domains in Kellum and Schedl, Cell 64:941–950 (1991).

MARs are in general AT rich by approximately 70% and are preferentially bound and cleaved by topoisomerase II. However, there is no consensus sequence known for MARs. The topoisomerase II consensus derived from Drosophila and vertebrates is only loosely-defined. A specialized DNA structure formed by certain AT rich sequences may be important for their biological function. The significance of structural characteristics for MAR such as DNA bending and a narrow minor groove due to oligo(dA) tracts has been previously proposed.

By employing an unpaired DNA-specific probe, chloroacetaldehyde (CAA)(Kohwi-Shigematsu et al., Proc. Natl Acad. Sci. (U.S.A.) 80:4389–4393 (1983); Kohwi-Shigematsu and Kohwi, Cell 43:199–206 (1985)) it has been demonstrated that naturally occurring MARs from different species are characterized by their strong potential for extensive base-unpairing, or unwinding, when subjected to superhelical strain (Kohwi-Shigematsu and Kohwi, Biochem. 29:9551–9560 (1990)). This unwinding property was shown to be important for binding to the nuclear matrix and for the augmentation of gene expression in stable transformants (Bode et al., Science 255:195–197 (1992)).

For example, two MARs flanking the immunoglobulin heavy chain (IgH) gene enhancer described in Cockerill, et al., J. Biol. Chem. 262:5394–5397 (1987), continuously unpaired over a distance of more than 200 base-pairs in supercoiled plasmid DNA. A short sequence motif, ATATAT, within the MAR located 3' of the IgH enhancer was delineated to be a nucleation site for unwinding. Point mutations substituting three bases in this sequence completely abolished the unwinding property of the MAR. In a subsequent study (Bode et al., (1992) supra.), it was shown that a concatemerized, double-stranded 25 base pair oligonucleotide containing the unwinding core sequence of the 3' MAR behaved like a typical MAR. This synthetic MAR was capable of unwinding under superhelical strain, strongly bound to the nuclear matrix with an affinity comparable to that observed with the 2 kilobase MAR from the human β-interferon (huIFN-b) gene, and enhanced transcription of a linked reporter gene in stable transformants. However, none of these features were observed with a similarly concatemerized, double-stranded oligonucleotide derived from the mutated core sequence: the unpairing property was lost, the binding affinity to the nuclear matrix was greatly reduced, and no enhancement of transcription was detected.

The unwinding property of MARs may be important in effectively relieving negative superhelical strain that could accumulate in a looped DNA domain and in preventing its influence on neighboring domains. If certain AT rich sequences are biologically significant due to their intrinsic structural property, it would be advantageous to identify a protein that recognizes and distinguishes AT rich sequences than can unwind from those that cannot unwind. Such a protein could be a MAR-binding protein. Except for topoisomerase II, little is known about scaffold proteins in higher eukaryotes. Recently, a MAR-binding protein, ARBP (Attachment Region Binding Protein), that binds to MARs from different species has been purified from chicken oviduct. However, a gene for ARBP has not yet been reported.

Thus, a need exists for identifying MAR binding proteins and nucleic acids encoding such proteins. The present invention satisfies this need and provides related advantages as well.

SUMMARY OF THE INVENTION

The present invention generally relates to a novel human protein that binds matrix/scaffold-associating DNA regions (MARs). The novel human protein, designated SATB1, is predominantly expressed in the thymus as a 85.9 kD protein. The SATB1 cDNA encodes a 763 amino acid sequence protein that is capable of binding to special AT rich sequences (ATC sequences). The invention further provides antibodies specifically reactive with such protein.

Isolated nucleic acids encoding the novel MAR-binding protein are also provided, as well as vectors containing the nucleic acids and recombinant host cells transformed with such vectors. The invention further provides methods of detecting such nucleic acids by containing a sample with a nucleic acid probe having a nucleotide sequence capable of hybridizing with the isolated nucleic acids of the present invention. Such probes can correspond to the ATC sequences.

BRIEF DESCRIPTION OF THE FIGURES

FIG. 4 shows the results of the missing nucleoside experiment of the SATB1-Wild-Type $(25)_2$ Complex.

(FIG. 4B) SATB1 contact sites on the oligomer wild-type $(25)_2$ were deduced from densitometer scans of the autoradiograms shown in (A) and are given by vertical bars. The height of the bars approximates the relative strength of the contacts between protein and individual nucleosides. Nucleosides with no indication were not contacted. Stars indicate adenines that interfered slightly with protein binding when methylated (see FIG. 7C).

FIG. 6 shows the ATC sequences and SATB1 contact sites in the IgH Enhancer Fragment.

(FIG. 6A) ATC sequences within the 5' and 3' regions of the IgH enhancer fragment are indicated by capital letters and brackets and their positions are shown by arabic numbers. (SEQ. ID. NO. 15, position 41–93; SEQ. ID. NO. 16, position 274–342; and SEQ ID. NO. 17, positions 731–807). The six SATB1 contact sites are underlined and indicated by roman numerals.

FIG. 7 shows the results of the distamycin A competition of SATB1 binding and chemical interference experiments.

FIG. 9 shows tissue specificity of SATB1 expression.

DETAILED DESCRIPTION OF THE INVENTION

Figure 1:
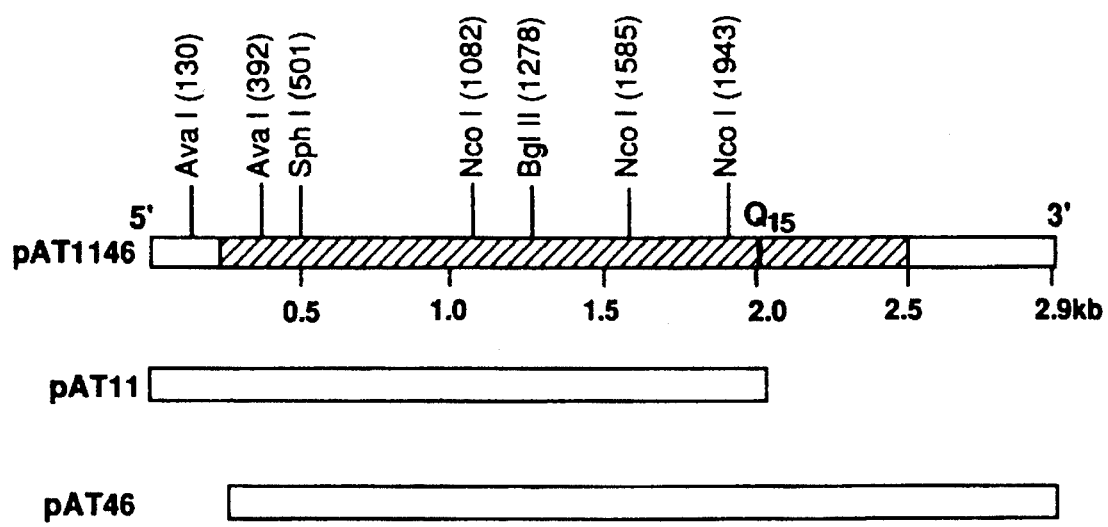
FIG. 1 shows the structural analysis of cloned SATB1 cDNA. Schematic structure of cDNA clone pAT1146, which was derived from pAT11 and pAT46 The hatched area represents the open reading frame. The solid bar indicates the glutamine stretch ($Q_{15}$) in the deduced amino acid sequence. Major restriction endonuclease sites are indicated.

The present invention generally relates to a novel human tissue specific MAR-binding protein designated herein as SATB1. This novel protein was discovered during studies that were initiated based on an idea that DNA with an unusual structural property could be specifically recognized by a cellular protein, not via its primary sequence, but through a sequence-directed structural distortion. The existence of such a protein would provide compelling evidence for the biological significance of an unusual DNA structure.

To this end, an AT-rich sequence previously determined to be the unwinding core element of a MAR segment located 3' of the IgH enhancer, as reported in Kohwi-Shigematsu and Kohwi, Biochemistry 29:9551–9560 (1990) and incorporated herein by reference, was selected as a potential protein binding site. Employing a concatemerized oligonucleotide of this sequence as a probe that behaves like a naturally occurring MAR as described in Bode et al., Science 255:195–197 (1992), incorporated herein by reference, a novel human cDNA of 2.9 Kb in length that encodes a 763 amino acids having a relative molecular weight of about 85.9 kD protein was isolated and characterized. SATB1 binds strongly to this probe, which readily unwinds when subjected to superhelical strain, but does not bind to the mutated probe that resists unwinding. Previous studies have produced results indicating that MARs have a high unwinding potential as a common structural property in Kohwi-Shigematsu and Kohwi (1990), supra, and Bode et al. (1992), supra.

Not only does SATB1 bind to the synthetic MAR probe, it also binds with high affinity to various MARs from human, mouse, Drosophila, yeast and plant. In addition, the SATB1 binding can be specifically competed by MARs from any species, but not by non-MAR DNAs. SATB1 is therefore considered to be a MAR-binding protein. Consistent with this notion, SATB1 was found in the nuclear matrix fraction of thymocytes. However, there may be AT rich sequences that satisfy the criteria of an ATC sequence without necessarily being MARs.

Only a few MAR-binding proteins are known to date. Besides the chicken MAR binding protein ARBP, which is described in Von Kries et al., Cell 64:123–135 (1991), some proteins preferentially bind MARs, although the binding is not MAR specific. For example, topoisomerase II, the major structural component of interphase nuclei as well as of scaffolds in mitotic chromosomes, preferentially binds MARs over non-MARs. RAP-1, a yeast protein, which was originally identified as the silencer binding protein in Shore and Nasmyth, Cell 51:721–732 (1987), is a yeast scaffold component that binds to MARs near the mating-type locus HML and forms DNA loops in vivo. Non-core histone H1 binds to DNA of varying sequences, but preferentially assembles on MARs under cooperative binding conditions.

None of the proteins described above, however, are related to SATB1. In fact, no amino acid sequences or nucleotide sequences homologous to SATB1 or its cDNA have been reported to date. The only exception is the stretch of glutamine residues in SATB1, which is found in other proteins. However, the function of the stretch of glutamine residues is unclear. A polyglutamine tract of 12 residues is present in the yeast DNA-binding protein datin, which recognizes oligo(dA)·oligo(dT) sequences according to reports published in Winter and Varshavsky, EMBO J. 8:1867–1877 (1989). Glutamine repeats were also identified in many homeobox genes of Drosophila (McGinnis et al., Nature 308:428–433 (1984); Wharton et al., Cell 40:55–62 (1985); and Frigerio et al., Cell 47:735–746 (1986)) and Xenopus (Sharpe et al., Cell 50:749–758 (1987). In addition, glutamine-rich regions are often found in the activation domain of transcription factors (Courey and Tjian, Cell 887–898 (1988)) including the human transcription factor IID (.Peterson et al., *Science* 248:1625–1630 (1990)). No amino acid or nucleotide sequence data is available for the chicken MAR binding protein ARBP (von Kries et al., *Nucl. Acids Res.* 18:3881–3885 (1991)). It appears however that SATB1 is not the human version of ARBP because a single prominent protein (presumably a human version of ARBP) that binds the chicken MAR probe was detected in HeLa cells from which SATB1 is absent. Moreover, ARBP-like proteins are found in many tissues, compared to SATB1, which is predominantly found in the thymus.

Although MARs are generally known to be AT-rich in general, the MAR binding protein SATB1 is not merely an AT-rich sequence binding protein. The studies relating to the present invention revealed a very high selectivity for only certain subsets of AT-rich sequences. Using SATB1 as a new tool, several features of the sequences that constitute MARs were discovered. For example, SATB1 showed a strong affinity to the double stranded, linear wild-type $(25)_7$ oligonucleotide that has a high potential to unwind under superhelical strain. In contrast, SATB1 exhibits a substantially low affinity to the mutated $(24)_8$ sequence with three base changes and one base deletion that leads to a complete loss of the unwinding property. Thus, specific point mutations that dramatically altered the structural property, but not significantly the overall AT content of the DNA, were clearly distinguished by SATB1. This result strongly suggests that the consensus for SATB1 binding is different from the primary base sequence which is commonly known as the criteria for recognition by most sequence-specific DNA binding proteins.

In addition, specific recognition by SATB1 was further demonstrated by the fact that among the 997 bp-IgH enhancer region containing two sets of MARs, only certain sets of short motifs in the MARs made direct contact with SATB1.. Regions of conjunctional SATB1-binding sites correspond to the sequences that have a potential to unwind or to the CAA-reactive sites in supercoiled DNA, as reported in Kohwi-Shigematsu and Kohwi (1990), supra.

None of these direct contact sites revealed a primary base sequence consensus. However, when these sites were compared in their natural sequence context, a common feature was found. That is, in addition to being AT rich, there is a bias in the distribution of cytosines or guanines on either strand. Such special AT rich sequences (referred to herein as "ACT sequences"), with one strand consisting exclusively of A's, T's, and C's, that are well mixed, avoiding long stretches of homopurines-homopyrimidines, confer SATB1 binding. The 30 bp-SAT sequence for contact site I in the 5' region of IgH enhancer is only 66% AT rich. Mutations that destroyed the SAT feature for site I but kept the direct contact site intact, severely reduced SATB1 binding. ATC sequences appear to be as specific as primary sequence consensus. ACT sequences thus represent a novel concept for protein binding consensus. A loosely defined consensus which could be drawn by aligning SATB1 direct contact sequences, as is generally done for other DNA binding proteins, would have been misleading in terms of defining binding specificity. The ATC sequence concept derived from SATB1 binding studies together with CAA-reactivity serves to better understand the nature of MAR sequences which otherwise are merely generally AT rich sequences without an obvious consensus. By examining other MARs from human, mouse, Drosophila, plant and yeast, it has been found that all of them, without exception, contain clusters of SAT sequences.

Within the mouse IgH enhancer region, only the ATC sequences that are clustered have the potential to become unpaired when subjected to superhelical strain. This conclusion is fully supported by another MAR model. The longest ATC sequence within an ATC cluster in the 800 bp core region of the huIFN-b MAR was delineated to be the unwinding core element, and mutation of this site abolished extensive unwinding of this MAR (Bode et al., (1992) supra) and led to reduction in the affinity to the nuclear matrix (Mielke et al., *Biochem* 29:7475–7485 (1991)). SATB1 binding-oligonucleotides that are selected from a pool of random synthetic oligonucleotides over several rounds of gel-shift assays have been studied. Preliminary results indicate that the sequences selected by SATB1 are predominantly ATC sequences. The results from this experiment should provide more detailed information about the sequence characteristics required for binding and the biological function of ATC sequences.

SATB1 also exhibits unusual binding characteristics. SATB1 binding has a high sequence selectivity and yet apparently makes little contact with the DNA bases. None of the chemical modifications at the major groove or depurination of approximately one base per molecule interfered with binding. The findings that (1) SATB1 did not bind in the major groove, (2) the missing nucleoside experiment revealed specific contact sites for SATB1 binding, and (3) the minor groove-binding distamycin inhibited SATB1 binding strongly suggest that SATB1 binds in the minor groove and recognizes ATC sequences indirectly through their effects on the geometry of the sugar-phosphate backbone. SATB1 seems to recognize a sequence dependent distortion of the DNA structure that already exists in the linear double-stranded DNA, presumably at the phosphate backbone and the minor groove, before the DNA sequence becomes unpaired as a result of superhelical strain. Unlike an autonomously replicating sequence (ARS) consensus-binding protein (ACBP) described in Hofmann and Gasser, *Cell* 64:951–960 (1991), SATB1 does not bind single-stranded SAT sequences.

It is known that most DNA binding proteins that have an obvious primary sequence consensus make contacts with the DNA bases in the major groove, whereas many proteins with low sequence selectivity, like the hemolytic unit class of proteins, histone H1, topoisomerase II, DNase I and the non-histone chromosomal α protein or HMG-I, which is part of the nuclear matrix, contact the phosphate backbone and the minor groove of DNA. Unlike these proteins, minor groove binding SATB1 is highly sequence selective.

The trp repressor is an example of a sequence-specific protein that interacts with the phosphate backbone but not directly with the DNA bases. This binding mode is similar to that of SATB1 in the sense that sequence recognition is indirectly achieved by the DNA structure. An important difference, however, is that SATB1 binds in the minor groove, while trp repressor binds in the major groove.

Some known sequence-specific binding proteins bind in the minor groove. Integration Host Factor (IHF) recognizes specific DNA sites as described in Goodrich et al., *Nucl. Acids Res.* 18:4993–5000 (1990), and yet it primarily contacts the minor groove of DNA. Transcription factor IID has a similar mode of binding: it binds to the TATA box, or the consensus 5' TATAAA 3' (Breathnach and Chambon, *Ann. Rev. Biochem.* 50:349–383 (1981)) in the minor groove. Both IHF and TFIID proteins, however, bind deeply in the minor groove so that they make direct contact with the bases.

In contrast, SATB1 binding in the minor groove hardly touches DNA bases except for two adenines. Furthermore, although substitutions of adenine to inosine, together with thymine to cytosine, within the direct contact site did not alter binding of TFIID (Starr and Hawley, *Cell* 67:1231-1240 (1991)), these substitutions diminished SATB1 binding. These substitutions can cause conformational changes of DNA, and therefore the minor groove conformation specifically determined by unsubstituted, natural ATC sequences must be important for SATB1 binding.

It is generally thought that MAR-binding proteins are structural components of the operationally defined nuclear matrix, and that they would play a role in Anchoring the bases of chromatin loops to the nuclear matrix. Thus, it has been natural to assume that MAR binding proteins are present in all cell types. Unexpectedly, the MAR binding protein SATB1 was found to be expressed predominantly in thymus, although present in minute quantity in other tissues. Therefore, SATB1, which is found in the nuclear matrix fraction of thymocytes, is the first tissue-specific MAR binding protein isolated and characterized.

It is believed that SATB1 might be involved in the regulation of gene expression. Preliminary studies show that indeed SATB1 acts as a suppressor for transcription based on transient cotransfection assays with a reporter gene. SATB1 may suppress a specific gene or multiple genes at the level of whole transcriptional domains, which may be possible by interacting with the bases of chromatin loops. The possibility that SATB1 regulates specific genes or specific transcriptional domains suggests other proteins may exist that interact with SATB1 to confer specificity to certain subsets of MARs. Alternatively, certain MARs with a much higher binding affinity to SATB1 than other MARs may exist in vivo. The finding of SATB1 raises the possibility that there might be other MAR-binding proteins that play a regulatory role in other tissues. The presence of other MAR-binding proteins is probable because MARs are often found in close vicinity or co-map with regulatory regions including enhancers. It is believed SATB1 represents a new class of regulatory proteins that exert their influence at the level of whole transcriptional domains rather than individual genes.

The cDNA of SATB1 has been cloned and isolated. The cDNA was cloned as described in Example I. It is believed that the cloning of the SATB1 gene represents an advancement in identifying the first example of a tissue-specific MAR-binding protein and in further understanding the function of MAR-binding proteins in general.

The present invention accordingly provides a purified human protein that binds a matrix/scaffold-associating DNA region (MAR). The purified protein has a relative molecular weight of about 85.9 kDa deduced from, the cDNA encoded protein and verified by SDS-PAGE under reducing conditions following conventional procedures.

As used herein, the terms "purified" and "isolated" mean that the molecule or compound is substantially free of contaminants normally associated with a native or natural environment. For example, a purified protein can be obtained from a number of methods. The naturally-occurring protein can be purified by any means known in the art, including, for example, by affinity purification with antibodies having specific reactivity with the protein. In this regard, anti-SATB1 antibodies can be used to substantially purify naturally-occurring SATB1 from thymocytes. Alternatively, a purified protein of the present invention can also be obtained by well known recombinant methods as described, for example, in Maniatis et al., *Molecular Cloning: A Laboratory Manual* 2d ed. (Cold Springs Harbor Laboratory 1989), which is incorporated herein by reference, and by the methods described in the Examples below. In addition, purified proteins can also be synthesized by methods known in the art.

The cDNA described in Example I encodes a protein having the 763 amino acid sequence (SEQ. ID. NO. 2) identified in Table 1. The nucleic acid sequence encoding the 763 amino acid protein (SEQ. ID. NO. 1) is also identified in Table 1.

TABLE 1

GGGGGGAAAGGAAAATAATACAATTTCAGGGGAAGTCGCCTTCAGGTCTGCTGCTTTTTTATTTTTTTTTTTTAATTAA  80

AAAAAAAAAGGACATAGAAAACATCAGTCTTGAACTTCTCTTCAAGAACCCGGGCTGCAAAGGAAATCTCCTTTGTTTTT  160

GTTATTTATGTGCTGTCAAGTTTTGAAGTGGTGATCTTTAGACAGTGACTGAGTATGGATCATTTGAACGAGGCAACTCA  240

M D H L N E A T O  9

GGGGAAAGAACATTCAGAAATGTCTAACAATGTGAGTGATCCGAAGGGTCCACCAGCCAAGATTGCCCGCCTGGAGCAGA  320

G K E H S E M S N N V S D P K G P P A K I A R L E O  35

ACGGGAGCCCGCTAGGAAGAGGAAGGCTTGGGAGTACAGGTGCAAAAATGCAGGGAGTGCCTTTAAAACACTCGGGCCAT  400

N G S P L G R G R L G S T G A K M O G V P L K H S G H  62

CTGATGAAAACCAACCTTAGGAAAGGAACCATGCTGCCAGTTTTCTGTGTGGTGGAACATTATGAAAACGCCATTGAATA  480

L M K T N L R K G T M L P V F C V V E H Y E N A I E Y  89

TGATTGCAAGGAGGAGCATGCAGAATTTGTGCTGGTGAGAAAGGATATGCTTTTCAACCAGCTGATCGAAATGGCATTGC  560

D C K E E H A E F V L V R K D M L F N O L I E M A L  115

TGTCTCTAGGTTATTCACATAGCTCTGCTGCCCAGGCCAAAGGGCTAATCCAGGTTGGAAAGTGGAATCCAGTTCCACTG  640

L S L G Y S H S S A A O A K G L I O Y G K W N P V P L  142

TCTTACGTGACAGATGCCCCTGATGCTACAGTAGCAGATATGCTTCAAGATGTGTATCATGTGGTCACATTGAAAATTCA  720

S Y V T D A P D A T V A D M L O D V Y H A V V T L K I O  169

TABLE 1-continued

```
GTTACACAGTTGCCCCAAACTAGAAGACTTGCCTCCCGAACAATGGTCGCACACCACAGTGAGGAATGCTCTGAAGGACT    800
   L   H   S   C   P   K   L   E   D   L   P   P   E   O   W   S   H   T   T   V   R   N   A   L   K   D     195
TACTGAAAGATATGAATCAGAGTTCATTGGCCAAGGAGTGCCCCCTTTCACAGAGTATGATTTCTTCCATTGTGAACAGT    880
   L   L   K   D   M   N   O   S   S   L   A   K   E   C   P   L   S   O   S   M   I   S   S   I   V   N   S   222
ACTTACTATGCAAATGTCTCAGCAGCAAAATGTCAAGAATTTGGAAGGTGGTACAAACATTTCAAGAAGACAAAAGATAT    960
   T   Y   Y   A   N   V   S   A   A   K   C   O   E   F   G   R   W   Y   K   H   F   K   K   T   K   D   M   249
GATGGTTGAAATGGATAGTCTTTCTGAGCTATCCCAGCAAGGCGCCAATCATGTCAATTTTGGCCAGCAACCAGTTCCAG   1040
       M   V   E   M   D   S   L   S   E   L   S   O   O   G   A   N   H   V   N   F   G   O   O   P   V   P   275
GGAACACAGCCGAGCAGCCTCCATCCCCTGCGCAGCTCTCCCATGGCAGCCAGCCCTCTGTCCGGACACCTCTTCCAAAC   1120
   G   N   T   A   E   Q   P   P   S   P   A   Q   L   S   H   G   S   Q   P   S   V   R   T   P   L   P   N    302
CTGCACCCTGGGCTCGTATCAACACCTATCAGTCCTCAATTGGTCAACCAGCAGCTGGTGATGGCTCAGCTGCTGAACCA   1200
   L   H   P   G   L   V   S   T   P   I   S   P   Q   L   V   N   Q   L   V   M   A   Q   L   L   N   Q   329
GCAGTATGCAGTGAATAGACTTTTAGCCCAGCAGTCCTTAAACCAACAATACTTGAACCACCCTCCCCCTGTCAGTAGAT   1280
       Q   Y   A   V   N   R   L   L   A   Q   Q   S   L   N   Q   Q   Y   L   N   H   P   P   P   V   S   R    355
CTATGAATAAGCCTTTGGAGCAACAGGTTTCGACCAACACAGAGGTGTCTTCCGAAATCTACCAGTGGGTACGCGATGAA   1360
   S   M   N   K   P   L   E   Q   Q   V   S   T   N   T   E   V   S   S   E   I   Y   Q   W   V   R   D   E    382
CTGAAACGAGCAGGAATCTCCCAGGCGGTATTTGCACGTGTGGCTTTTAACAGAACTCAGGGCTTGCTTTCAGAAATCCT   1440
   L   K   R   A   G   I   S   Q   A   V   F   A   R   V   A   F   N   R   T   Q   G   L   L   S   E   I   L   409
CCGAAAGGAAGAGGACCCCAAGACTGCATCCCAGTCTTTGCTGGTAAACCTTCGGGCTATGCAGAATTTCTTGCAGTTAC   1520
       R   K   E   E   D   P   K   T   A   S   Q   S   L   L   V   N   L   R   A   M   Q   N   F   L   Q   L    435
CGGAAGCTGAAAGAGACCGAATATACCAGGACGAAAGGGAAGGAGCTTGAATGCTGCCTCGGCCATGGGTCCTGCCCCC   1600
   P   E   A   E   R   D   R   I   Y   Q   D   E   R   E   R   S   L   N   A   A   S   A   M   G   P   A   P   462
CTCATCAGCACACCACCCAGCCGTCCTCCCCAGGTGAAAACAGCTACTATTGCCACTGAAAGGAATGGGAAACCAGAGAA   1680
   L   I   S   T   P   P   S   R   P   P   Q   V   K   T   A   T   I   A   T   E   R   N   G   K   P   E   N   489
CAATACCATGAACATTAATGCTTCCATTTATGATGAGATTCAGCAGGAAATGAAGCGTGCTAAAGTGTCTCAAGCACTGT   1760
       N   T   M   N   I   N   A   S   I   Y   D   E   I   Q   Q   E   M   K   R   A   K   V   S   Q   A   L    515
TTGCAAAGGTTGCAGCAACCAAAAGCCAGGGATGGTTGTGCGAGCTGTTACGCTGGAAAGAAGATCCTTCTCCAGAAAAC   1840
   F   A   K   V   A   A   T   K   S   Q   G   W   L   C   E   L   L   R   W   K   E   D   P   S   P   E   N   542
AGAACCCTGTGGGAGAACCTCTCCATGATCCGAAGGTTCCTCAGTCTTCCTCAGCCAGAACGTGATGCCATTTATGAACA   1920
   R   T   L   W   E   N   L   S   M   I   R   R   F   L   S   L   P   Q   P   E   R   D   A   I   Y   E   Q   569
GGAGAGCAACGCGGTGCATCACCATGGCGACAGGCCGCCCCACATTATCCATGTTCCAGCAGAGCAGATTCAGCAACAGC   2000
   E   S   N   A   V   H   H   H   G   D   R   P   P   H   I   I   H   V   P   A   E   Q   I   Q   Q   Q        595
AGCAGCAACAGCAACAGCAGCAGCAGCAGCAGCAGGCACCGCCGCCTCCACAGCCACAGCAGCAGCCACAGACAGGCCCT   2080
   Q   Q   Q   Q   Q   Q   Q   Q   Q   Q   Q   Q   A   P   P   P   P   Q   P   Q   Q   Q   P   Q   T   G   P   622
CGGCTCCCCCCACGGCAACCCACGGTGGCCTCTCCAGCAGAGTCAGATGAGGAAAACCGACAGAAGACCCGGCCACGAAC   2160
   R   L   P   P   R   Q   P   T   V   A   S   P   A   E   S   D   E   E   N   R   Q   K   T   R   P   R   T   649
AAAAAATTTCAGTGGAAGCCTTGGGAATCCTCCAGAGTTTCATACAAGACGTGGGCCTGTACCCTGACGAAGAGGCCATCC   2240
   K   I   S   V   E   A   L   G   I   L   Q   S   F   i   Q   D   V   G   L   Y   P   D   E   E   A   I       675
AGACTCTGTCTGCCCAGCTCGACCTTCCCAAGTACACCATCATCAAGTTCTTTCAGAACCAGCGGTACTATCTCAAGCAC   2320
   Q   T   L   S   A   Q   L   D   L   P   K   Y   T   I   I   K   F   F   Q   N   Q   R   Y   Y   L   K   H   702
CACGGCAAACTGAAGGACAATTCCGGTTTAGAGGTCGATGTGGCAGAATATAAAGAAGAGGAGCTGCTGAAGGATTTGGA   2400
   H   G   K   L   K   D   N   S   G   L   E   V   D   V   A   E   Y   K   E   E   E   L   L   K   D   L   E   729
```

TABLE 1-continued

```
AGAGAGTGTCCAAGATAAAAATACTAACACCCTTTTTTCAGTGAAACTAGAAGAAGAGCTGTCAGTGGAAGGAAACACAG  2480
  E   S   V   O   D   K   N   T   N   T   L   F   S   V   K   L   E   E   E   L   S   V   E   G   N   T          755
ACATTAATACTGATTTGAAAGACTGAGATAAAAGTATTTGTTTCGTTCAACAGTGCCACTGGTATTTACTAACAAAATGA  2560
  D   I   N   T   D   L   K   D                                                                                    763
AAAGTCCACCTTGTCTTCTCTCAGAAAACCTTTGTTGTTCATTGTTTGGCCAATGAATCTTCAAAAACTTGCACAAACAG  2640
AAAAGTTGGAAAAGGATAATACAGACTGCACTAAATGTTTTCCTCTGTTTTACAAACTGCTTGGCAGCCCCAGGTGAAGC  2720
ATCAAGGATTGTTTGGTATTAAAATTTGTGTTCACGGGATGCACCAAAGTGTGTACCCCGTAAGCATGAAACCAGTGTTT  2800
TTTGTTTTTTTTTTAGTTCTTATTCCGGAGCCTCAAACAAGCATTATACCTTCTGTGATTATGATTTCCTCTCCTATAAT  2880
TATTTCTGTAGCACTCCACACTGATCTTTGGAAACTTGCCCCTTATTTAAAAAAAAAAAAAAAAAAA  2946
```

As used herein, the term "substantially the sequence" includes the described nucleotide or amino acid sequence and sequences having one or more additions, deletions or substitutions that do not substantially affect the ability of the sequence to encode a protein having a desired activity. Thus, sequence modifications that do not substantially alter such activity are intended. For example, a protein having substantially the amino acid sequence of SEQ. ID. NO. 2 refers to SATB1 encoded by the cDNA described in Example I as well as proteins having amino acid sequences that are modified but, nevertheless, retain the functions of SATB1. One skilled in the art can readily determine such retention of function following the guidance set forth herein.

The present invention is further directed to active fragments of the human tissue-specific MAR-binding protein. As used herein, an active fragment refers to portions of the protein that substantially retains the MAR-binding activity of the intact protein. One skilled in the art can readily identify active fragments of proteins such as SATB1 by comparing the activities of a selected fragment with the intact protein following the guidance set forth in the Examples below.

Multiple discrete SATB1-binding sequences with the IgH enhancer have been identified as described in Example VII. Such sequences are listed in Table 2.

TABLE 2

SATB1 Binding Contact Sites

| Site | Sequence | Residue Numbers | SEQ. ID.NOS. |
|---|---|---|---|
| I | 3'-ATAATCTTC-5' | (69–77) | 3 |
| II | 5'-AATAATAAAT-3' | (293–302) | 4 |
| III | 5'-ATATTTTT-3' | (303–320) | 5 |
| IV | 5'-TTCTAATATAT-3' | (740–750) | 6 |
| V | 5'-AATAATAGAGTAATTTT-3' | (765–781) | 7 |
| VI | 5'-ACCAATAATCA-3 | (790–800) | 8 |

These direct contact sequences contain no sequence homology among themselves except for their high AT content. However, they are examples of ATC sequences since they exhibit stretches of AT-rich sequences with an asymmetric distribution of guanine/cysteine residues between the two strands.

As noted previously, the proteins of the present invention bind in the minor groove of double-stranded DNA without directly contacting any bases other than the two adenine residues. The fact that SATB1 recognizes only ATC sequences and binds in the minor groove without extensive base contacts indicates that sequence recognition is determined indirectly by a specific structure of the sugar-phosphate backbone in the minor groove at specific sets of AT-rich sequences in double stranded DNA.

Relatedly, the invention also provides isolated nucleic acids encoding the human tissue-specific MAR-binding protein identified above. The nucleic acids can be in the form of DNA, RNA or cDNA, such as the novel cDNA of 2.9 kb identified in Table 1 for example. Such nucleic acids can also be chemically synthesized by methods known in the art, including, for example, the use of an automated nucleic acid synthesizer.

The nucleic acid can have substantially the nucleotide sequence identified in Table 1 (SEQ. ID. No. 1). Portions of such nucleic acids that encode active fragments of the MAR-binding protein of the present invention are also contemplated.

Nucleic acid probes capable of hybridizing to the nucleic acids of the present invention under reasonably stringent conditions can be prepared from the cloned sequences or by synthesizing oligonucleotides by methods known in the art. The probes can be labeled with markers according to methods known in the art and used to detect the nucleic acids of the present invention. Methods for detecting such nucleic acids can be accomplished by contacting the probe with a sample containing or suspected of containing the nucleic acid under hybridization conditions, and detecting the hybridization of the probe to the nucleic acid.

The present invention is further directed to vectors containing the nucleic acids described above. The term "vector" includes vectors that are capable of expressing nucleic acid sequences operably linked to regulatory sequences capable of effecting their expression. Numerous cloning vectors are known in the art. Thus, the selection of an appropriate cloning vector is a matter of choice. In general, useful vectors for recombinant DNA are often plasmids, which refer to circular double stranded DNA loops such as pAT1146. As used herein, "plasmid" and "vector" may be used interchangeably as the plasmid is a common form of a vector. However, the invention is intended to include other forms of expression vectors that serve equivalent functions.

Suitable host cells containing the vectors of the present invention are also provided. Host cells can be transformed with a vector and used to express the desired recombinant or fusion protein. Methods of recombinant expression in a variety of host cells, such as mammalian, yeast, insect or bacterial cells, are widely known. For example, a nucleic acid encoding the MAR-binding protein can be transfected into cells using the calcium phosphate technique or other transfections methods such as those described in Maniatis et al., *Molecular Cloning: A Laboratory Manual* 2d ed. (Cold Springs Harbor Laboratory 1989), which is incorporated herein by reference.

Alternatively, nucleic acids can be introduced into cells by infection with a retrovirus carrying the gene or genes of interest. For example, the gene can be cloned into a plasmid containing retroviral long terminal repeat sequences (LTRs), the gene encoding the MAR-binding protein, and an antibiotic resistance gene for selection. The construct can then be transfected into a suitable cell line, such as PA12, which carriers packaging deficient provirus and expresses all of the necessary components for virus production, including synthesis of amphotrophic glycoproteins. The supernatant from these cell contain infectious virus which can be used to infect the cells of interest.

Also provided are antibodies having specificity reactivity with the MAR-binding proteins of the present invention, such as anti-SATB1 antibodies. Active fragments of antibodies, for example, Fab and Fab'$_2$ fragments, having specificity reactivity with such proteins are intended to fall within the definition of an "antibody." Antibodies exhibiting a titer of at least about $1.5 \times 10^5$ as determined by ELISA are useful in the present invention.

The antibodies of the invention can be produced by any method known in the art or by the method described in Example XIII. For example, polyclonal and monoclonal antibodies can be produced by methods known in the art, and as described, for example, in Harlow and Lane, *Antibodies: A Laboratory Manual* (Cold Spring Harbor Laboratory 1988), which is incorporated herein by reference. The proteins, particularly SATB1, of the present invention can be used as the immunogen in generating such antibodies. Altered antibodies, such as chimeric, humanized, CDR-grafted or bifunctional antibodies can also be produced by methods well known to those skilled in the art. Such antibodies can also be produced by hybridoma, chemical synthesis or recombinant methods described, for example, in Maniatis et al., supra, incorporated herein by reference.

The antibodies can be used for determining the presence or purification of the MAR-binding proteins of the present invention. With respect to the detecting of such proteins, the antibodies can be used for in vitro diagnostic or in vivo imaging methods. For the in vitro diagnostic methods, a tissue sample obtained from a subject can be contacted with an antibody of the present invention and the binding of the antibody to the target protein is thereafter detected by any suitable means known in the art.

Immunological procedures useful for the in vitro detection of the target MAR binding protein in a sample include immunoassays that employ a detectable antibody. Such immunoassays include, for example, ELISA, agglutination assays, flow cytometry, serum diagnostic assays, immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

For the in vivo imaging methods, a detectable antibody can be administered to a subject and the binding of the antibody to the MAR-binding protein can be detected by imaging techniques well known in the art. Suitable imaging agents are known and include, for example, gamma-emitting radionuclides such as $^{111}$In, $^{99m}$Tc, $^{51}$Cr and the like, as well as paramagnetic metal ions, which are described in U.S. Pat. No. 4,647, 447, incorporated herein by reference. The radionuclides permit the imaging of tissues or organs by gamma scintillation photometry, positron emission tomography, single photon emission computed tomography and gamma camera whole body imaging, while paramagnetic metal ions permit visualization by magnetic resonance imaging.

The present invention further provides methods of inhibiting the growth of cells, such as tumor cells, by introducing a nucleic acid encoding the proteins of the present invention into the cells. As described in Example XVII, cells having been transfected with vectors containing such nucleic acids have died very quickly. Thus, the results suggest that these methods provide an effective means for inhibiting the growth of tumors, such as, for example, during the early stage of leukemia.

The invention also provides gene therapy for the treatment of tumorigenicity by introducing a nucleic acid encoding SATB1 or other tissue-specific MAR-binding protein into a vector and administering the vector to a subject. More specifically, the method involves (a) selectively introducing into a tumor cell a nucleic acid encoding the tissue-specific MAR-binding protein of the invention operationally linked to expression elements; and (b) expressing the nucleic acid within the tumor cell wherein the expression level of the encoded gene is increased.

Several methods of introducing expression vectors encoding the desired protein into tumorigenic cells are available. One skilled in the art would readily know such methods in addition to identifying the method most well suited for the intended application. For example, populations of specific lymphocytes can be selected after culturing the cells from a subject by fluorescent activated cell sorting (FACS) using an antibody specific for the cell type. The cell population can then be stably transfected with expression vectors containing SATB1 cDNA and transplanted into the subject's bone marrow.

Alternatively, retroviral systems can be used to specifically target SATB1 cDNA to specific cell types. Retroviruses infect specific cell types by recognizing specific cell surface components. Such systems advantageously exhibit the horizontal infectivity characteristics of natural retroviruses without promoting diseases or onocogenesis.

Another alternative involves globally introducing the SATB1 cDNA-containing vectors into a larger population of cells within the organism where the elements directing cDNA expression function only in the desired population of cells. For example, using a promoter that is active only in T cells to direct cDNA expression allows introduction of the vector into all blood lineages with specific expression only in T cells.

Pharmaceutical compositions containing pharmaceutically-acceptable carriers and MAR-binding proteins, nucleic acids or antibodies of the present invention useful for imaging or therapy can be prepared by methods known in the art, including the simple mixing of reagents. Such carriers are well known and include, for example, aqueous solutions such as bicarbonate buffers, phosphate buffers, Ringer's solution and physiological saline. Those skilled in the art will know that the choice of the pharmaceutical carrier and the appropriate preparation of the composition will depend on the intended use and mode of administration.

The dosage regimen for the in vivo diagnostic and therapeutic methods depends on a variety of factors, including the age, weight, and medical condition of the subject, as well as the type of disorder, the severity of the condition, the route of administration and the diagnostic or therapeutic agent used. A skilled physician or veterinarian can readily determine and prescribe an effective amount of the compound or pharmaceutical composition required.

Finally, kits useful for carrying out the methods of the invention are also provided. The kits can contain a MAR-binding protein, antibody or nucleic acid of the present invention and an ancillary reagent. Such ancillary reagents include diagnostic or therapeutic agents, signal detection systems, buffers, stabilizers, pharmaceutically acceptable carriers or other reagents and materials conventionally included in such kits.

The following examples are intended to illustrate but not limit the present invention.

EXAMPLE I cDNA Cloning of a 85.9 Kd MAR-binding Protein

The wild type (25 bp) and mutant (24 bp) oligonucleotides containing the wild type or mutated sequence derived from the MAR 3' of the mouse immunoglobulin heavy chain (IgH) gene enhancer (position 731–756) were synthesized, made into duplex DNA and multimerized to either dimers, pentamers, heptamers or octamers as described (Bode et al., 1992). In brief, complementary oligonucleotides for the wild type (25 bp), 5'-TCTTTAATTTCTA ATATATTTAGAAttc-3' (SEQ. ID. NO. 9) and 5'-TTCTAAATATATTAGAAATTAAAGAgaa-3' (SEQ. ID. NO. 10), containing the nucleation site for base-unpairing (underlined) (Kohwi-Shigematsu and Kohwi, 1990) were hybridized into double-stranded DNA concatemerized by hybridization through overlapping single-stranded ends (indicated by small letters) to seven repeats so that their orientation of the sequence was the same throughout the multimer. The single-stranded ends of multimers were digested with mung bean nuclease. Multimers were separated on a polyacrylamide gel, and cloned into the EcoRV site of a Bluescript vector. The concatemerized sequences were isolated by digesting the Bluescript recombinant DNA with BamHI and HindIII. The resulting wild type $(25)_7$ exhibited the following features: strong base-unpairing property under superhelical strain; high affinity to the nuclear matrix; and an ability to enhance transcription when linked to a reporter gene in stable transformants as described in Bode et al, (1992) supra.

The cloned wild-type $(25)_7$ was excised from the vector Bluescript by BamHI-HindIII digestion and end-labeled with the DNA polymerase I Klenow fragment to a specific activity of $4\times10^8$ cpm/µg. It was used as a probe to screen protein replica filters of a human testis cDNA λgt11 library prepared from human testis RNA (provided by Dr. Jose Millan, La Jolla Cancer Research Foundation). Plating of the library and screening of the filters was done as described by Vinson et al., Genes Dev. 2:801–806 (1988), incorporated herein by reference, except that the filter overlays were incubated at room temperature overnight and the guanidine hydrochloride denaturation/renaturation cycles were omitted. Binding reactions were carried out at 4° C. for 3 hours, the binding buffer was supplemented with 10 µg/ml poly (dI-dC), 10 µg/ml denatured salmon sperm DNA and 125 mM NaCl. Screening of 500,000 phage plaques yielded one clone, λAT11, containing an insert of 2 kilobases (kb) in length, which expressed a protein that bound to the DNA probe. The phage clone λAT11, was further purified through four successive round of filter hybridizations and its insert was subcloned in the EcoRI site of the vector Bluescript (pAT11) and sequenced (FIG. 1).

Because of the absence of a complete 3' end, the same library was rescreened with the pAT11 cDNA insert and five additional clones were isolated. These were sequenced and all five clones were found to be homologous to pAT11. cDNA clones were digested from both 5'- and 3'-ends with exonuclease III/mung bean nuclease to generate overlapping deletion clones. Sequencing was performed with modified T7 DNA Polymerase (Pharmacia) according to the manufacturer's instructions.

One clone, pAT46, contained a poly(A) tail, but was 300 bp shorter than pAT11 at the 5' end. The overlapping sequences of pAT11 and pAT46 were confirmed to be identical. A full-length cDNA in Bluescript vector (pAT1146) was generated by replacing the BglII-XbaI fragment of pAT11 cDNA in the Bluescript by the BglII-XbaI fragment of pAT46. The complete 2946 bp nucleotide sequence of pAT1146 is shown in Table 1. It includes a short, AT-rich 5' untranslated region (215 nucleotides), followed by an ATG codon that meets the criteria for translation initiation as described in Kozak, Nucl. Acids Res. 12:857–872 (1984), followed by a long open reading frame of 763 amino acids, that encodes a protein of 85.9 kilodaltons (Kd), referred to as SATB1 (special AT-rich sequence binding protein 1).

The coding sequence is followed by a long 3' untranslated region, (444 nucleotides) which includes a poly$(A)_{18}$ tail. From a mouse cDNA library, a cDNA from a single clone encodes a 764 amino acid protein that is 98% homologous to human SATB1 at the nucleotide sequence level. This finding confirms that the fused pAT1146 cDNA represents a naturally occurring human cDNA.

Except for the presence of a continuous stretch of 15 glutamine residues at the carboxy terminal (residues 592 to 607) (Table 1), the deduced amino acid sequence does not contain any obvious sequence motifs such as zinc fingers, leucine zippers or helix-turn-helix domains. Basic and acidic amino acids are evenly distributed throughout the 763 amino acids of the protein. Computer assisted comparison of SATB1 to the Genbank and NBRF database revealed no homologous sequences, except for the glutamine stretch, indicating that this protein is a novel DNA-binding protein.

EXAMPLE II

In Vitro Transcription

In vitro transcription reactions were done with 1 µg of linearized, proteinase K treated plasmid DNA with a purchased RNA synthesis kit (Stratagene, San Diego, Calif.). The quality of the synthesized RNA was examined by formaldehyde agarose gel electrophoresis as described in Maniatis, et al. supra and the yield was determined by $OD_{260}$ measurement.

Protein was synthesized from 0.5 µg RNA/50 µl reaction in a rabbit reticulocyte lysate system (Promega) with [$^{35}$S] -methionine. The full-length SATB1 was produced from the T3 promoter of pAT1146 linearized with BamHI. The 3' deletions ΔAT11, ΔBglII and ΔNcoI were generated with T3 RNA polymerase from pAT11 which was cut with BamHI (polylinker), BglII (1270) and NcoI (1982), respectively. Deletion Δ12 was obtained by exonuclease III/mung bean nuclease digestion of pAT11, cut at the BamHI (polylinker) site. The shortened fragment was digested at the 5' end with EcoRI, purified and subcloned into EcoRI-HincII cut Bluescript. For in vitro transcription, this plasmid was linearized at the XhoI site of the polylinker and T7 RNA polymerase was used for sense-RNA synthesis.

To confirm that the protein size predicted from the cDNA corresponded to the size of the expressed protein, the cDNA was placed under control of the T7 RNA polymerase promoter and RNA was synthesized and translated in vitro in reticulocyte lysate. Proteins were separated on SDS-polyacrylamide minigels (SDS-PAGE) by the method of Laemmli, *Nature* 227:680–685 (1970), incorporated herein by reference, and the bacterially produced proteins were visualized by staining the gels with Coomassie brilliant blue, whereas the [$^{35}$S]-labeled proteins produced in reticulocyte lysate were exposed to XAR film. Protein concentrations were determined using a protein assay kit (Bio-Rad, Richmond, Calif.). Analysis of the translation products on an SDS-polyacrylamide gel revealed a major band of approximately 90 Kd which is in agreement with the predicted size.

EXAMPLE III

Sequence Selectivity for SATB1 Binding

To examine whether SATB1 has sequence selectivity among different AT rich sequences, cDNA clone SATB1 was tested for its ability to distinguish the wild type $(25)_7$ sequence described above from a similarly concatemerized mutated DNA, mut $(24)_8$, prepared from oligonucleotide 5'-TCTTTAATTTCTA<u>CTGCT</u>TTAGAAttc-3' (SEQ. ID. NO. 11) and its complementary sequence, in which the ATATAT motif in the wild type oligonucleotide was replaced by the underlined sequence. In contrast to wild type $(25)_7$, the mutant $(24)_8$ totally resisted unwinding under superhelical strain even though it is still AT rich. Binding of SATB1 to the wild type and mutated oligonucleotide sequences was studied by mobility shift assays with bacterially produced SATB1. The DNA sequence of a single repeating unit for each type of DNA is shown in Table 3.

TABLE 3

| | 3' | 5' | |
|---|---|---|---|
| WT: | TCTTTAATTTCTAATATATTTAGAA | | (SEQ. ID. NO. 9) |
| MUT: | TCTTTAATTTCTACTG–CTTTAGAA | | (SEQ. ID. NO. 12) |

Binding reactions were done in 10 µl total volume containing 10 mM Hepes pH 7.9, 1 mM DTT, 50 mM KCl, 2.5 mM MgCl2, 10% glycerol, 0.1 mg/ml poly(dI-dC)·poly(dI-dC) and 0.5–1 µg thrombin cleaved 80 Kd-ΔSATB1 described in Example V, or 1 µl of the reticulocyte lysate reaction containing in vitro synthesized SATB1. When purified fusion protein was used, the reaction mixture was supplemented with 5 mg/ml bovine serum albumin. Samples were preincubated at room temperature for 5 minutes before radiolabeled DNA probe (0.5 ng) was added. In some cases, 100 ng of unlabeled DNA probe was added as a specific competitor. The binding reaction was allowed to proceed at room temperature for 15 minutes. Aliquots (4 µl) of each sample were electrophoresed at 120 V for 2 hours through a 6% acrylamide minigel (8×10 cm), containing 0.05% bisacrylamide, 5% glycerol and 0.5× TBE (Maniatis, 1982). The gels were dried onto Whatman 3 MM paper and exposed to XAR film. Two films were superimposed to distinguish the [$^{35}$S]-methionine labeled protein from the [$^{32}$P]-labeled DNA.

Figure 3:
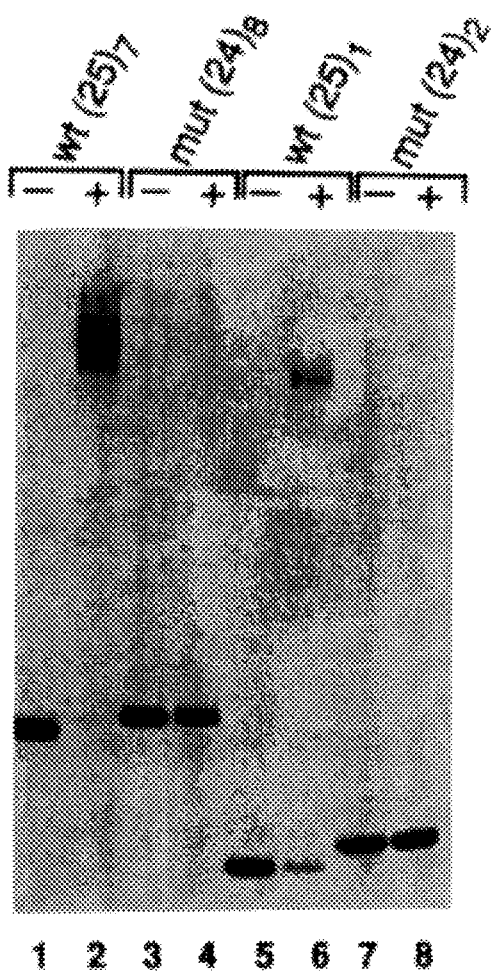
FIG. 3 shows the sequence requirement for SATB1 binding. Autoradiograph of a gel retardation assay with SATB1, synthesized in reticulocyte lysate, and various repeats of wild-type or mutated synthetic oligonucleotide probes. Lanes 1 and 2: wild-type $(25)_7$; lanes 3 and 4: mutated $(24)_8$; lanes 5 and 6: wild-type $(25)_1$; lanes 7 and 8: mutated $(24)_2$. Odd numbered lanes (−) are controls without added protein; even numbered lanes (+) contain SATB1, synthesized in reticulocyte lysate.

Probes used in gel-mobility shift assays were generated by cutting plasmids with appropriate restriction enzymes, purifying the fragments from agarose or polyacrylamide gels and end-labeling with DNA polymerase I Klenow fragment by standard procedures described in Maniatis et al., supra (FIG. 3).

The wild type $(25)_7$ probe, which was used to isolate the SATB1 cDNA in the first place, was strongly complexed by SATB1 (FIG. 3, lane 2). A monomer of the same sequence also bound to SATB1, although the affinity was somewhat reduced (FIG. 3, lane 6). The mutant sequence however, did not bind, even when it was concatemerized to eight or two repeats (FIG. 3, lanes 4 and 8). Therefore, the previously defined nucleation site for base-unpairing important for MAR binding and transcriptional activation, was successfully distinguished by SATB1 from the AT rich, mutated version. Unlike other AT rich sequence binding proteins such as a protein, an HMG protein, which binds to any runs of six or more AT base pairs, SATB1 binding clearly shows a high sequence selectivity among AT rich sequences.

EXAMPLE IV

The DNA Binding Domain of SATB1

Figure 2:
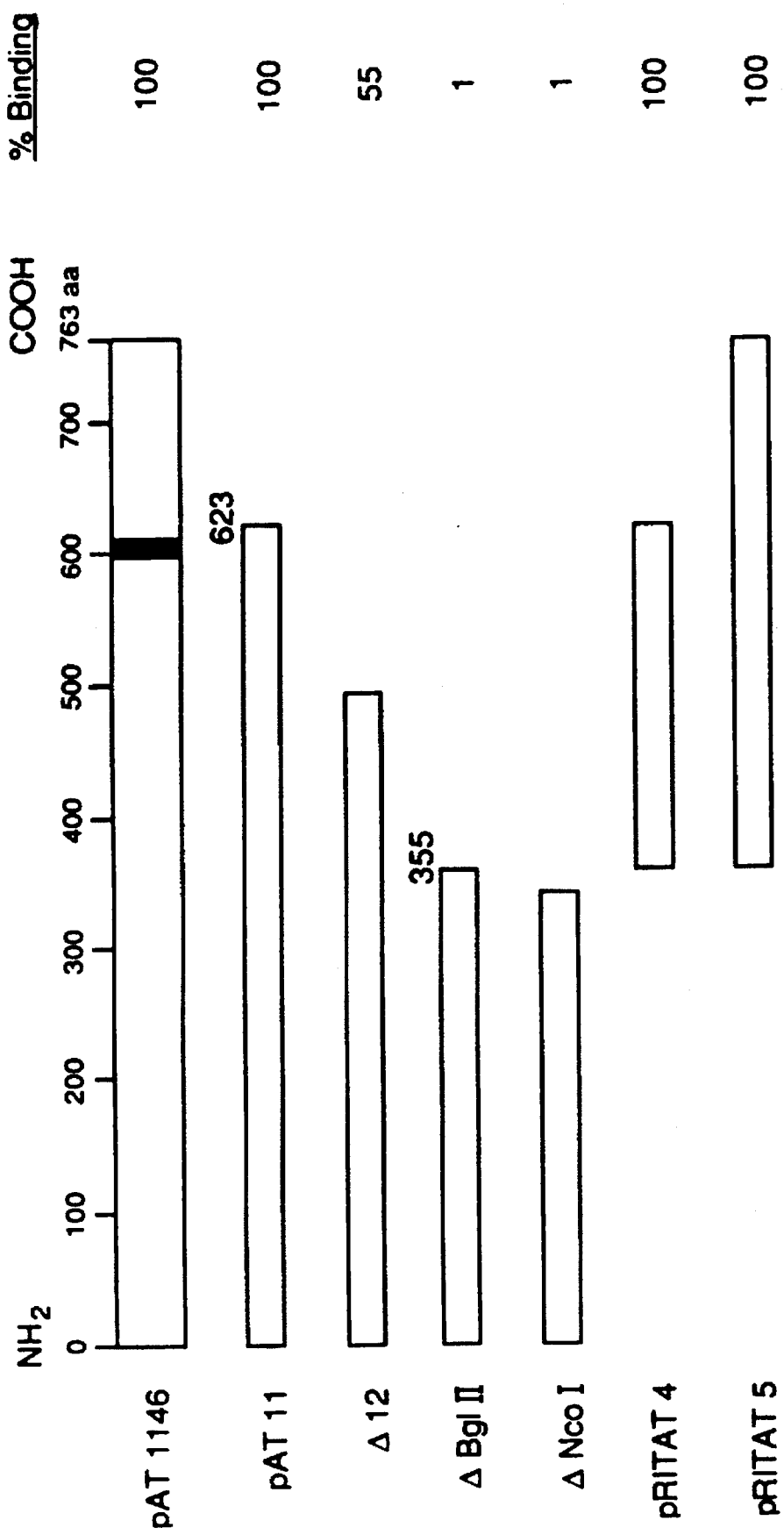
FIG. 2 shows the mapping of the DNA-binding domain of SATB1. Plasmids expressing SATB1 and its deletion mutants were constructed and are indicated on the left of the diagram. Schematic representation of SATB1 and deletion mutants. The full-length SATB1 and the COOH-terminal deletions derived from plasmids pAT1146, pAT11, $\Delta$12, $\Delta$BglII and $\Delta$NcoI were synthesized in vitro using a rabbit reticulocyte system. The two NH$_2$-terminal deletions derived from pRITAT 4 and pRITAT 5, were protein A—fusion proteins. The glutamine stretch in the amino acid sequence is indicated by a black box. Relative binding activities (%) were calculated by densitometry scanning of autoradiographs from gel retardation assays.

In order to identify the region of the protein responsible for DNA binding, a series of C-terminal and N-terminal deletions of SATB1 were made, that were expressed either in reticulocyte lysate (C-terminal deletions), or as protein A-fusion proteins in *E. coli* (N-terminal deletions) (FIG. 2). The binding activities of the full-length and truncated proteins were tested in gel-mobility shift assays. Under the conditions employed, the full-length SATB1 protein (763 amino acids) bound completely (100%) to the wild-type $(25)_7$ probe leaving no free probe. The same 100% shift was achieved with the pAT11 protein, in which 140 C-terminal amino acids were deleted but the glutamine-tract was still present. Binding activity was reduced to 55% with deletion protein Δ12, which lacks 265 C-terminal residues including the glutamine-tract. Deletion clones ΔBgl II (408 amino acids deleted) and ΔNcoI (446 amino acids deleted) exhibited virtually no binding activity. These results define the binding domain of SATB1 between amino acid residue 355 and 623. Although the glutamine-tract is included in the binding domain, it does not seem to be mandatory for binding.

EXAMPLE V

Expression of SATB1

Protein A-ΔSATB1 fusion proteins were prepared by subcloning the 3'BglII(1270)-BamHI(polylinker) fragments of the cDNA clones pAT11 and pAT1146 (see FIG. 2) in the BamHI site of the protein A expression vector pRIT-2T (Pharmacia). The resulting recombinant plasmids were designated pRITAT4 and pRITAT5, respectively. Protein was synthesized for 3 hours at 42° C. following the manufacturer's instructions. Cells were disrupted by sonication and the protein A-ΔSATB1 fusion protein was partially purified on an IgG Sepharose Fast Flow affinity column (Pharmacia). Bacterially produced protein A-fusion proteins RITAT4, containing residues 355 to 623 and RITAT5, containing residues 355 to 763, where the N-terminal 355 amino acid residues of SATB1 have been deleted in both cases were also tested. Both proteins showed a binding activity of 100%, as judged from mobility shift assays, the result of which confirms the binding domain determined above.

EXAMPLE VI

Identification of Nucleosides Contacted by SATB1

To determine the sequences that make contact with SATB1, DNase I footprinting was attempted using the dimerized wild type $(25)_2$. However, regions protected by SATB1 from DNase I cleavage were undetectable, even though the probe was strongly bound by protein. The failure to obtain DNase I footprints was possibly due to the rapid on/off-rate of protein binding: under the DNase I footprinting assay conditions, the off-rate of SATB1 as determined according to Weeks and Crothers, Cell 66:577–588 (1991) was 1/min for the wild type $(25)_2$, and 0.3/min for the wild type $(25)_7$.

Therefore, the missing nucleoside experiment described by Hayes and Tullius, Biochem. 28:9521–9527 (1989), incorporated herein by reference, was adopted with minor modifications to determine which nucleosides are contacted by SATB1 on the DNA. Approximately 150 ng ($3 \times 10^6$ cpm) of a radiolabeled DNA fragment was used for hydroxyl radical treatment at 37° C. The final Fe(II) concentration was 20 μM. Binding reactions were carried out as described above, with 8 μg of thrombin cleaved 80Kd-ΔSATB1 and 50 ng ($10^6$ cpm) DNA probe in a total volume of 30 μl. Under these conditions, at least 75% of the labeled probe was routinely found to be shifted by protein after gel electrophoresis.

The protein-DNA complex and the remaining free probe were separated by polyacrylamide minigel electrophoresis and visualized by exposure of the wet gel to XAR film for 30 minutes at 4° C. Free and bound probes were eluted from the gel by soaking the gel slices containing the respective fragments overnight at 37° C. in 0.2M NaCl/TE, followed by purification through Elutip-D columns (Schleicher-Schuell), phenol/chloroform extraction and ethanol precipitation with 20 μg glycogen as a carrier. The purified DNA was electrophoresed through 8% denaturing polyacrylamide gels. Autoradiographs of the sequencing gels were scanned by laser densitometry to determine the relative strengths of contacts between SATB1 and the target DNA.

In this procedure, the hydroxyl radical cleavage reaction is used to generate DNA fragments which contain on average one random nucleoside gap per molecule. Hydroxyl radical treatment results in the loss of a deoxyribose residue with its attached base and causes the phosphodiester backbone to break at this position. The randomly gapped DNA fragments are used as probes in a standard chemical interference experiment. The wild type $(25)_2$ XbaI-HindIII fragment (cloned in Bluescript), was selectively labeled at the XbaI site either on the 3'-strand by Klenow polymerase, or on the 5'-strand by T4-polynucleotide kinase, and subjected to a limited hydroxyl radical treatment. The gapped DNA molecules were incubated with bacterially produced SATB1 in typical binding reaction, followed by the gel shift assay on a native polyacrylamide gel.

Figure 4A:
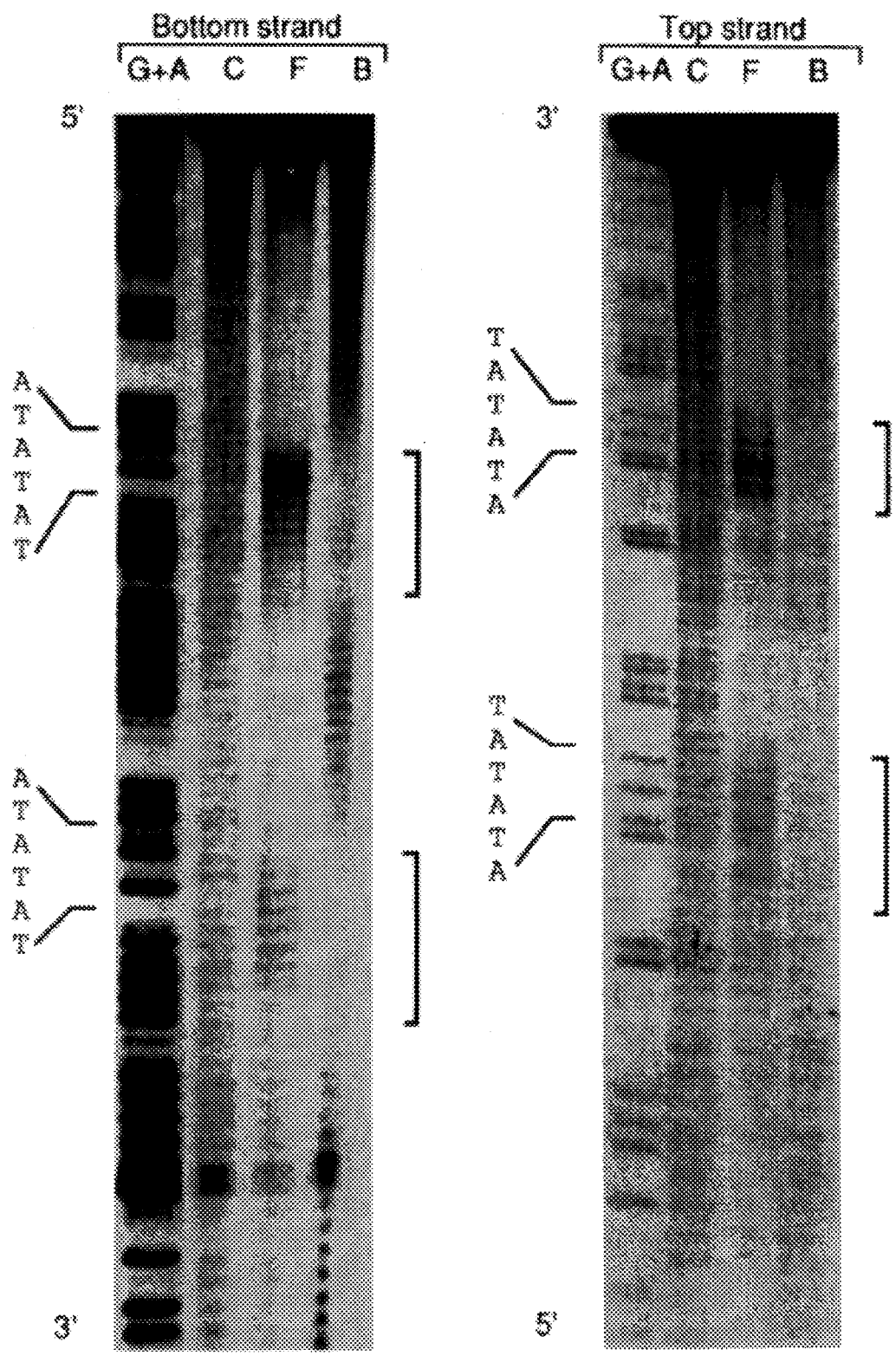
(FIG. 4A) Sequencing gel showing the products obtained from a missing nucleoside experiment. Bacterially produced SATB1 protein was bound to the hydroxyl radical-treated wild-type $(25)_2$, which was 5'-labeled by polynucleotide kinase (top strand, right panel), or 3'-labeled by DNA polymerase I Klenow fragment (bottom strand, left panel) at the XbaI site of the Bluescript polylinker. Lanes marked G+A represent Maxam-Gilbert G+A-specific sequencing reactions performed on the intact DNA fragment. The control lane C shows the hydroxyl radical cleavage pattern of the DNA probe in the absence of bound protein. Lanes F and B represent the free and protein-bound probes, respectively, that were separated in a gel mobility shift assay. Vertical brackets indicate nucleosides contacted by SATB1. The 5'-ATATAT-3' motif is indicated alongside the G+A ladder.

The free (non-shifted band) and bound DNA (shifted band) were purified and then run on a denaturing urea/polyacrylamide gel. An autoradiogram of a sequencing gel from one of these experiments is shown in FIG. 4A. Missing nucleosides essential for binding (marked by vertical brackets) are detected as low intensity or lacking bands in the lane that contains DNA bound to protein (lane B), or as high intensity bands in the lane that contains free, unbound probe (lane F). The control lane (C) contained naked DNA treated with hydroxyl radical which gave rise to a relatively even banding pattern. The bands of the autoradiogram were aligned to control bands corresponding to the G and A residues of the fragment (lane G+A), and scanned by laser densitometry.

The relative strength of the nucleoside contacts were estimated by comparing the relative peak heights of the densitometer scans and are summarized in FIG. 4B. The contact site spans about 11 nucleosides on each strand, the contacted region on the bottom strand is offset by one base to the 3' end. The strongest contacted motif is 5'TTCTAATATAT3' (SEQ. ID. NO. 6) on the top strand, and 5'TATATTAGAAA3' (SEQ. ID. NO. 4) on the bottom strand. This result shows that the six base-pairs motif ATATAT is located within the site contacted by SATB1, which is in agreement with the mutational analysis, but it seems not to be solely responsible for binding since neighboring sequences (towards the 5' end on the top strand and towards the 3' end on the bottom strand) are contacted just as strongly. An identical result summarized in FIG. 4B) was obtained for each of the two repeated sequences (FIG. 4A).

EXAMPLE VII

Multiple Discrete SATB1 Binding Sequences Within the IgH Enhancer

The XbaI restriction fragment (1-992) containing the entire IgH enhancer region as described in Gillies et al., Cell 33:717–728 (1983), incorporated herein by reference, was cloned by use of EcoRI linkers, in the EcoRI site of plasmid pUC18. The subfragments of the IgH enhancer region that were used in gel retardation assays were the following: 5'-En was a fragment located between XbaI(1) and PvuII(382), the core enhancer was excised by PvuII(382) and EcoRI(683) digestion, and the 3'-En spanned the region between EcoRI (683) and XbaI(992). The 5'-En and the 3'-En fragments were subcloned in the XbaI-HincII and EcoRI sites of the vector Bluescript (Stratagene), respectively. The wt51 and mut51 probes were prepared by hybridizing the oligonucleotide sequences shown in FIG. 6B, which contain the 5' most SATB1 contact site (site I) followed by purification from an acrylamide gel.

Figure 6B:
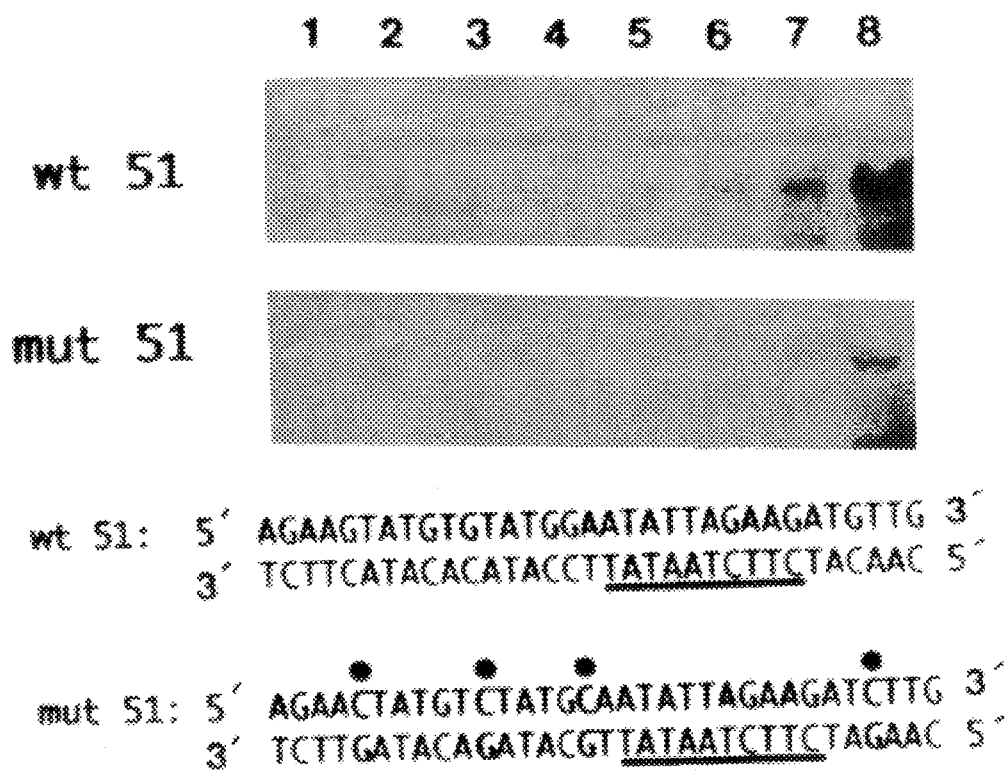
(FIG. 6B) Band shift assay with bacterially produced SATB1 and oligomers derived from the ATC sequence 51–83 (SEQ. ID. NO. 18, wt 51, and SEQ. ID. NO. 19, mut 51). Only the shifted bands are shown for better comparison between the wild-type (wt 51) and mutated (mut 51) ATC sequence 51 –83. Lanes 1–8 contain the following protein concentrations in ng: 0 (lane 1), 31 (lane 2), 62.5 (lane 3), 125 (lane 4), 250 (lane 5), 500 (lane 6), 1000 (lane 7), 2000 (lane 8). The sequences of the double-stranded oligomers wt 51 and mut 51 are shown at the bottom; the dots indicate G nucleotides that were replaced by C nucleotides in the mutated DNA. The SATB1 contact site is underlined.
Figure 6C:
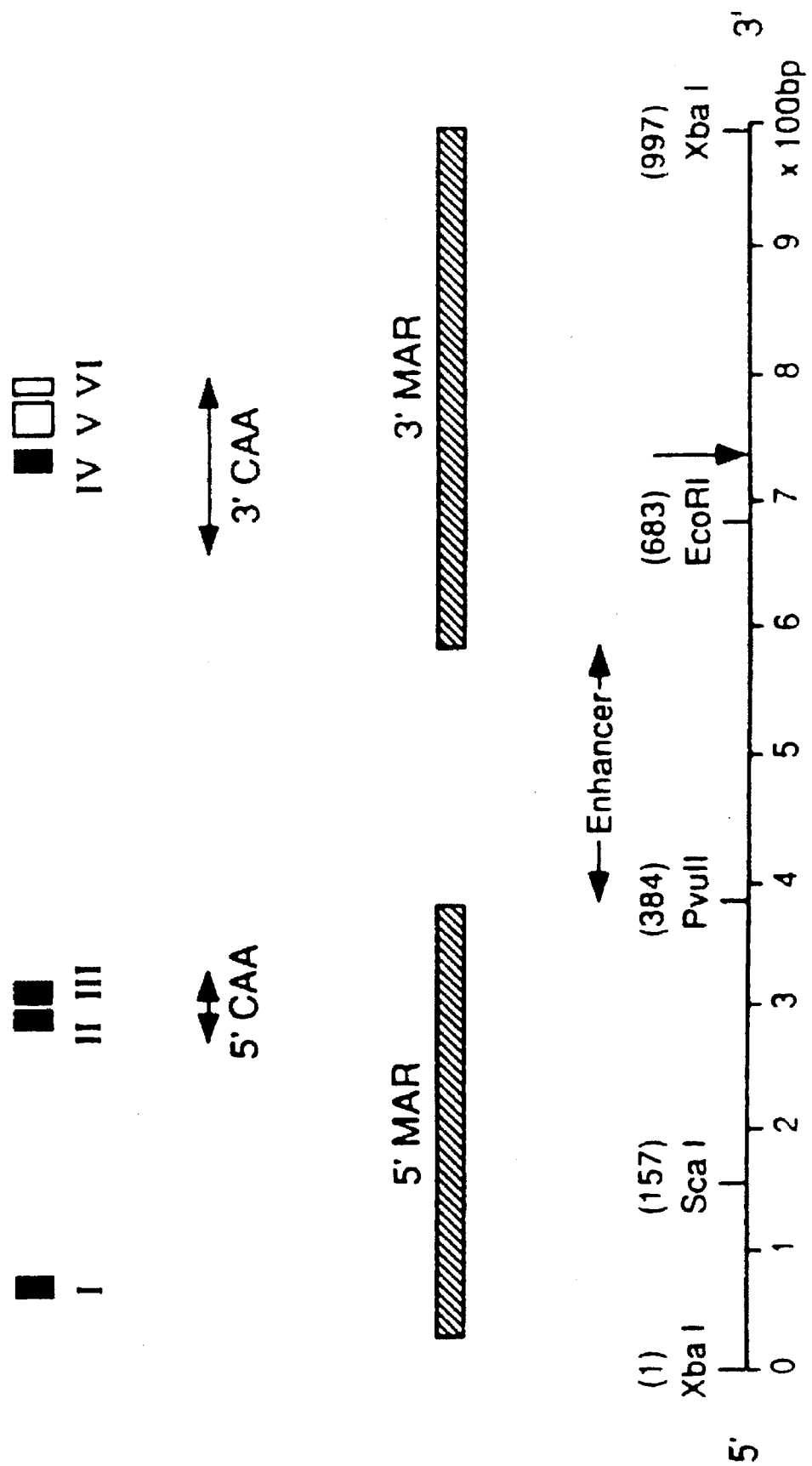
(FIG. 6C) Relative location of SATB1 binding sites and sequences with known activities in the IgH enhancer. The 997 bp XbaI fragment containing the enhancer, flanked by the 5' and 3' regions, is pictured with the major restriction sites. The arrow indicates the location of the ATATAT nucleation site for unpairing. The MARs located 5' and 3' of the enhancer core are shown by hatched bars. CAA-reactive areas are represented by double-headed arrows. The four major and two minor recognition sites for SATB1 are given by closed and open bars, respectively.

Mutation analysis revealed a certain sequence selectivity for SATB1 binding (FIG. 3). Potential SATB1 binding site(s) within the whole 997 bp IgH enhancer region were examined. The original 25 bp sequence used as a probe for SATB1 binding occurs only once in this region and is located 3' of the enhancer. Because the 997 bp XbaI fragment contains two sets of MARs surrounding the IgH enhancer as shown in Cockerill et al., J. Biol. Chem. 262:5394–5397 (1987), which coincide with the sequences that become unpaired and reactive with CAA under superhelical strain, SATB1 might also bind at multiple sites if it is a MAR binding protein (A map of the IgH enhancer fragment is shown in FIG. 6C).

Figure 5A:
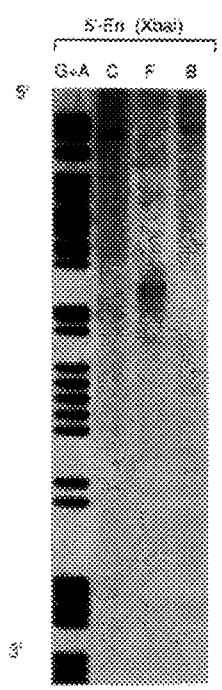
(FIG. 5A) and (FIG. 5B) The 5'-enhancer (5'-En) fragment [XbaI(1)-PvuII(384)] was subcloned in Bluescript and 3'-labeled with Klenow either at the BamHI site of the polylinker, which flanks the XbaI(1) site of the IgH enhancer fragment (FIG. 5A), or at the XhoI site of the polylinker, flanking the PvuII(384) site of the IgH enhancer (FIG. 5B).
Figure 5B:
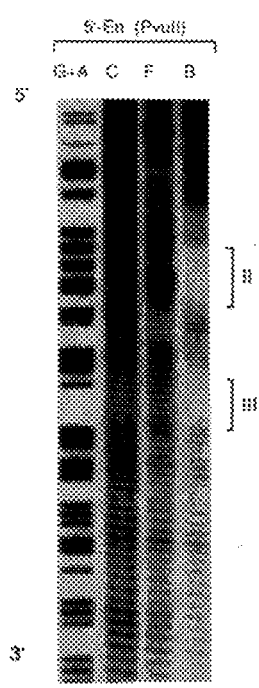
FIG. 5 shows the results of the missing nucleoside experiment of SATB1 bound to the IgH Enhancer Region. The missing nucleoside experiment was performed as described for FIG. 4. Annotations at the top of the lanes are identical to those in FIG. 4. Each autoradiograph shows the results obtained with restriction fragments derived from the enhancer 5'- and 3'-flanking regions as probes (for map see FIG. 6C).
(FIG. 5C) Wild-type 3'-enhancer (3'-En) region [EcoRI (683)-XbaI(997)], 5'-labeled with T4 polynucleotide kinase at the HindIII site of the Bluescript polylinker which is adjacent to EcoRI(683).
(FIG. 5D) Mutated 3'-enhancer fragment [EcoRI(683)-XbaI(997)] labeled with Klenow at the EcoRI(683) site. The roman numerals alongside vertical brackets indicate specific contact sites of protein with DNA. The sequences of these sites and their relative locations within the IgH enhancer fragment are given in FIG. 6.

The missing nucleoside mapping technique as described for the wild type $(25)_2$ was used to map precise contact regions within the 5'-enhancer fragment [XbaI(1)-PvuII (384)] and the 3'-enhancer fragment [EcoRI(683)-XbaI(997) ]. The numbering is according to Gillies et al., supra. Among the three DNA fragments, the core [PvuII(394)-EcoRI(683)] did not contain SATB1 binding sites, as determined by gel-mobility shift assay (data not shown). The results for the 5'-enhancer region employing the 384 bp 5' XbaI-PvuII fragment labeled at either end (FIGS. 5A and B) revealed three contact sites. Vertical brackets with roman numerals indicate site I that consists of 3'ATAATCTTC 5'(69–77) (FIG. 5A), site II and site III, which are 10 bp apart and correspond to 5'AATAATAAAT3' (293–302) and 5'ATATTTTT3' (313–320), respectively (FIG. 5B).

In the 314 bp EcoRI-3' XbaI restriction fragment containing the 3'-enhancer region, one major contact site (site IV) was found which corresponds to 5'TTCTAATATAT3'

Figure 5C:
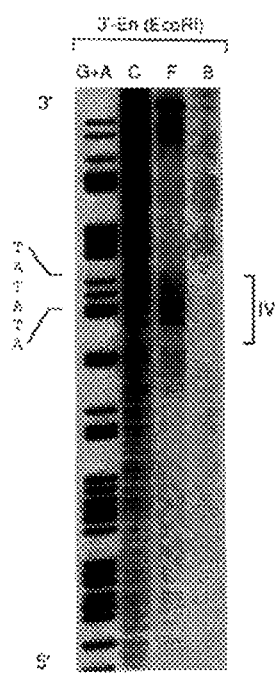
Figure 5D:
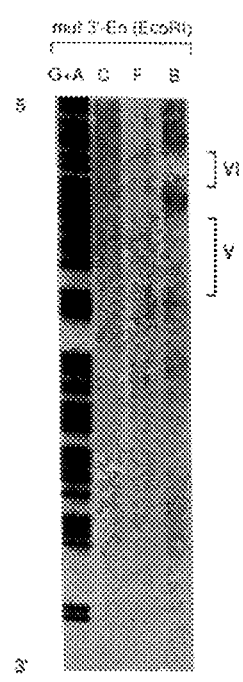

(740–750) (SEQ. ID. NO. 6) (FIG. 5C). As expected, site IV is identical to the contact site determined for the oligomer probe (FIG. 4C) containing this sequence. Although this SATB1 contact sequence, site IV, exhibits the strongest CAA-reactivity, a very high reactivity that persists at high salt was also detected in its immediate 3' neighboring sequence. When the major contact site IV was mutated in the same way as shown in FIG. 3B within the natural sequence context of the 314 bp EcoRI-3' XbaI fragment, the resulting DNA still retained SATB1 binding based on the gel-shift assay (data not shown). Therefore, it was determined whether SATB1 binding could also be detected in the neighboring sequences by employing the mutated 314 bp DNA in a hydroxyl radical interference experiment. Two additional contact sites were detected downstream of site IV, which were designated site V and site VI and consisted of 5'AATAATAGAGTAATTTT3' (765–781) (SEQ. ID. NO. 7) and 5'ACCAATAATCA3' (790–800) (SEQ. ID. NO. 8), respectively (FIG. 5D). These two sites appear to be low affinity binding sites, since they can only be detected by hydroxyl radical interference when the major site IV is destroyed.

EXAMPLE VIII

Special AT Rich Sequences Recognized by SATB1

When the direct contact sequences were compared, no sequence homology was found except for their high AT content. Nevertheless, SATB1 appears to be highly sequence selective as revealed by the fact that only a limited set of sequences were selected among approximately 750 bp of MAR regions delimited by Cockerill et al., supra. To better understand the basis for SATB1 recognition, the direct contact sequences in their natural sequence context (FIG. 6A) were compared. One common characteristic among these sequences was found: SATB1 contact sites are located in long runs of AT rich sequences with an asymmetric distribution of guanine residues between the two strands; one strand consists of C, A and T exclusively, and the other strand contains only G, T and A. A sequence having this characteristic is designated herein as a special AT rich sequence (ATC or SAT sequence), for convenience. To test whether the asymmetric distribution of C or G in one strand is important for SATB1 recognition, mutated DNA (shown in FIG. 6B) was used that was derived from the ATC sequence 51–83 (which includes site I) where the G nucleotides in the top strand were replaced with alternating G and C nucleotides throughout the ATC sequence, but the 10 bp-direct contact site was kept intact. As a result, four bases were mutated in the surrounding sequences among the 33 bp DNA containing the contact site. These changes in the base sequence greatly reduced the binding affinity to SATB1 as revealed by gel shift assays (FIG. 6B). This experiment strongly supports the concept that SAT sequence is SATB1 binding sequence consensus. This result also confirms that sequence recognition by SATB1 is mediated not only through the direct contact site, but also through the sequences immediately surrounding this site.

As summarized in FIG. 6C, the sites recognized by SATB1, or ATC sequences are clustered, and some are even superimposed (indicated by brackets in FIG. 6A) within the two matrix attachment regions surrounding the enhancer core (Cockerill et al., supra). These clustered AT sequences coincide with the CAA reactive regions described in Kohwi-Shigematsu and Kohwi, (1990), supra. The adjacent sites II and III correspond to the major CAA-reactive region 5' of the enhancer whereas the adjacent sites IV, V, and VI correspond to the CAA-reactive region 3' of the enhancer. Site I confers SATB1 binding but this region is not CAA-reactive. It appears that CAA-reactivity is predominantly found in the region where ATC sequences are clustered and a single, isolated ATC sequence like the one containing site I, does not confer CAA reactivity. For example, it was found that even the base-unpairing activity of site IV, which contains the nucleation sequence for unwinding, is greatly reduced when this site is placed by itself in a random sequence context.

EXAMPLE IX

SATB1 Binding in the Minor Groove of DNA With Little Contact with the Bases

For protein binding interference experiments, DNA probes were selectively labeled at one end by digesting the plasmid containing the respective fragment with an appropriate restriction enzyme, followed by labeling with the Klenow fragment at the 3' end of with T4-polynucleotide kinase at the 5' end after dephosphorylation with calf intestinal phosphatase. Unincorporated deoxyribonucleotides were removed by spin column chromatography through Sephadex G50, followed by a second restriction enzyme digestion at the opposite end of the probe. The labeled fragment was purified from a native polyacrylamide gel by electroelution into dialysis bags, or by soaking the gel slice in 0.2M NaCl TE at 37° C. overnight, and subsequent Elutip-D (Schleicher Schuell) purification.

There is a small group of DNA binding proteins reported to date that interact with AT rich sequences within the minor groove. This group includes *Escherichia coli* Integration Host Factor (IHF) protein and members of the eukaryotic High Mobility Group (HMG) family (reviewed in Churchill and Travers, *TIBS* 16:92–94 (1991)). Most recently, RNA polymerase II transcription factor TFIID was added to this list. To test whether SATB1 binds in the minor groove, distamycin A, which specifically binds minor grooves of AT-rich DNA (Coll et al., *Proc. Natl. Acad. Sci.(U.S.A.)* 84:8385–8389 (1987), was used as a competitor for SATB1 binding. The conformational effect on DNA exerted by distamycin is very small according to Kopka et al, *Proc. Natl Acad. Sci. (U.S.A.)*, 82:1376–1380 (1985) and Coll et al., supra.

Figure 7A:
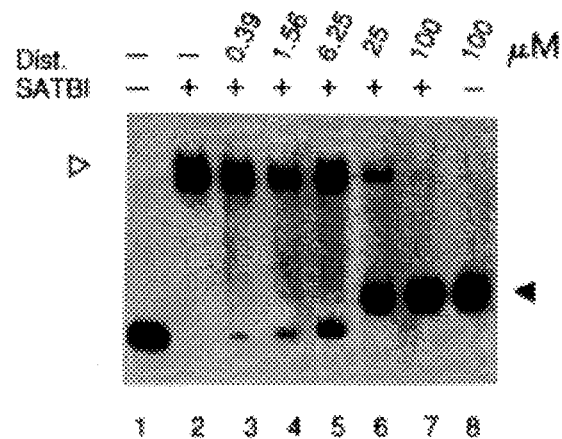
(FIG. 7A) Distamycin A competition: autoradiograph of a gel retardation assay with SATB1 synthesized in rabbit reticulocyte lysate and radiolabeled 3'-En fragment [EcoRI (683)-XbaI(997)]. Distamycin A (Dist.) was added at the start of the binding reaction at the concentrations indicated in µM at the top of the lanes. The open arrow head indicates SATB1 bound DNA and the solid arrow head indicates distamycin bound DNA. SATB1 was omitted or present in the samples indicated by (–) or (+), respectively.

Mobility shift assays showed that the quantitative binding of wild type $(25)_2$ to SATB1 in the absence of distamycin A (FIG. 7A, lane 2, indicated by open arrow) decreased with increasing distamycin A concentrations (lanes 3 to 7), until almost all the SATB1-DNA complex was ultimately replaced by a distamycin-DNA complex (indicated by a solid arrow) at 100 µM distamycin A (lane 8). Thus, distamycin A prevents binding of SATB1 to DNA in a concentration dependent manner, implying a minor groove recognition of SATB1. Similar results were obtained with a smaller minor groove binding drug, berenil (provided by Dr. Stephen Neidle), which is described in Brown et al., *EMBO J.* 9:1329–1334 (1990) and Laughton et al., *Nucl. Acids. Res.* 18:4479–4488 (1990).

For methylation interference experiments, a single end-labeled fragment ($7 \times 10^6$ cpm) was chemically modified with 1 µl dimethylsulfate in 200 µl total volume for 5 minutes at 15° C. according to Maxam and Gilbert, *Proc. Natl Acad. Sci. (U.S.A.)* 74(2):560–564 (1977). The subsequent band shift assay, the isolation and purification of the free and protein-bound probes were done exactly as described for the missing nucleoside experiment, except that the purified probes were cleaved with piperidine before loading on an 8% sequencing gel. This same procedure was used for the acid depurination interference experiments as described in Brunelle and Schleif, *Proc. Natl Acad. Sci. (U.S.A.)* 84:6673–6676 (1987), incorporated herein by reference, except that the target probe ($2 \times 10^6$ cpm in 15 μl) was treated with 1 μl of 4% formic acid for 25 minutes at 37° C. to partially eliminate guanines and adenines.

For CAA interference analysis, supercoiled pSERCμ300 bp containing the EcoRI(683) to XbaI(997) fragment of the IgH enhancer region was modified with CAA at 50 mM $Na^+$ concentration at pH 5 as described in Kohwi-Shigematsu and Kohwi (1990), supra. The extent and the site of modification was confirmed by the chemical cleavage method (Kohwi and Kohwi-Shigematsu, *Proc. Natl Acad. Sci. (U.S.A.)* 85:3781–3785 (1988). The CAA-modified EcoRI-XbaI fragment was used as a probe for protein binding.

Figures 7B, 7C:
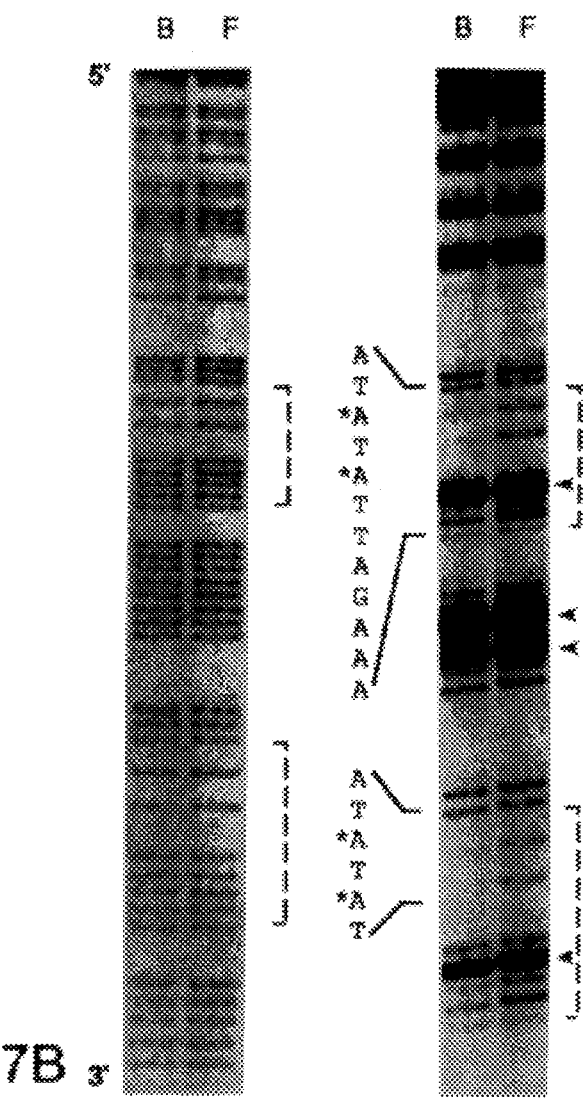
(FIG. 7B) Depurination interference and (C) Methylation interference with end-labeled [wild type $(25)_2$], bound to thrombin cleaved bacterially produced SATB1. Lane B, bound probe, lane F, free probe as described in FIG. 4 legend. The stippled bars indicate SATB1 contact sites as determined by hydroxyl radical interference, and the full contact sequence and the location of ATATAT sequence within the Other contact site are given in C. Two adenine residues in each repeat that interfered with binding when methylated are indicated by stars.

To determine whether SATB1 directly contacts specific bases, the wild type $(25)_2$ DNA was sparingly depurinated by formic acid and complexed with SATB1 under the same conditions employed for the hydroxyl radical interference assay which showed interference for binding. After binding with protein, free and protein-bound probes were isolated, cleaved with piperidine and separated on a sequencing gel to determine if depurination of certain nucleotides interfered with binding (Brunelle and Schleif, supra). This interference assay removes only the bases and is different from that with hydroxyl radical which removes both the bases and the sugar moieties. FIG. 7B shows that depurination did not interfere with SATB1 binding: band intensities in the purine ladders were identical for free and protein bound probes, even at the previously determined sites that interfered with binding after hydroxyl radical treatment (indicated by stippled brackets).

Chemical modifications of bases in the major groove also did not affect SATB1 binding. Methylation of the N-7 position of guanine residues by dimethylsulfate did not interfere with protein binding (FIG. 7C). CAA which specifically modifies N-6 and N-1 positions of adenine and N-3 and N-4 positions of cytosine residues were also used for interference assays and it was observed that CAA modification at the SATB1 contact site does not affect SATB1 binding. The minor groove modification at the N-3 position of adenine residues by dimethylsulfate did not show major interference with SATB1 binding (FIG. 7C). Only two modified adenine residues within the 11 bp contact site IV, which contains seven adenine residues, interfered slightly with protein binding, as revealed by reduced band intensities in the lane containing bound probe compared to the lane containing free probe.

It was concluded, from these results, that SATB1 binds along the minor groove of DNA without making direct contact with bases except for the two adenine residues. The results described above suggest an unusual mode of binding for SATB1: recognition of binding sites appears to be highly sequence selective, binding occurs in the minor groove, without extensive base contacts, indicting that the sequence recognition may be determined indirectly by a specific structure of the sugar-phosphate backbone in the minor groove at specific sets of AT rich sequences.

EXAMPLE X

Specific Binding of SATB1 to MAR Sequences from Different Species

The yeast histone H4 ARS is located on a HindIII(398)-EcoRI(798) restriction fragment derived from plasmid pAB9 (Bouton and Smith, *Mol. Cell Biol.* 6:2354–2363 (1986) gift of Dr. D. Kowalski. The centromere CENIII sequence was isolated as a 0.6 kb Sau3A fragment from plasmid pYE(CEN3)30 described in Fitzgerald-Hayes et al., *Cell* 29:235–244 (1982), gift of Dr. J. Carbon. The human IFN-β probe was a XmnI (564)-BamHI(995) fragment purified from plasmid pCL described in Klehr et al., *Biochem.* 30:1264–1270 (1991), gift of Dr. J. Bode. The human β-globin MAR fragment was located on a 300 bp HindIII-ApaLI fragment from plasmid pRYG described in Muller et al., *Biochem.* 27:8369–8379 (1988), gift of Dr. M. Muller. The plant MAR probe was a StyI(2643)-XbaI(3140) fragment isolated from the potato gene ST-LSI, in pUC19 described in Stockhaus et al., *Nucl. Acid Res.* 15:3479–3491 (1987), gift of Dr. J. Bode. A TATA box containing DNA sequence was isolated from the Ptac promoter of the vector pGEX-2T (Pharmacia) by SspI(164)-EcoNI(264) digestion. The poly$(dA)_{18}$ sequence in the BspEI(2826)-BamHI (polylinker) region of the cDNA clone pAT1146 was used as a probe. The synthetic oligonucleotides 32 bp-poly$(dA-dT)_n$, 33 bp-polyd$(dG-dA)_n$ and 31 bp-poly$(dA-dC)_n$ as well as the Oxytricha telomere sequence (gift of Dr. V. Zakian) were cloned in the polylinker of pUC19, and purified from the plasmids after EcoRI-HindIII digestion. The AT-rich spacer region from Xenopus oocyte 5S DNA was a 530 bp HaeIII-HindIII fragment from the cloned insert X1036 of the plasmid pMB9 gift of Dr. W. Reynolds and described in Fedoroff and Brown, *Cell* 13:701–716 (1978).

Figure 8:
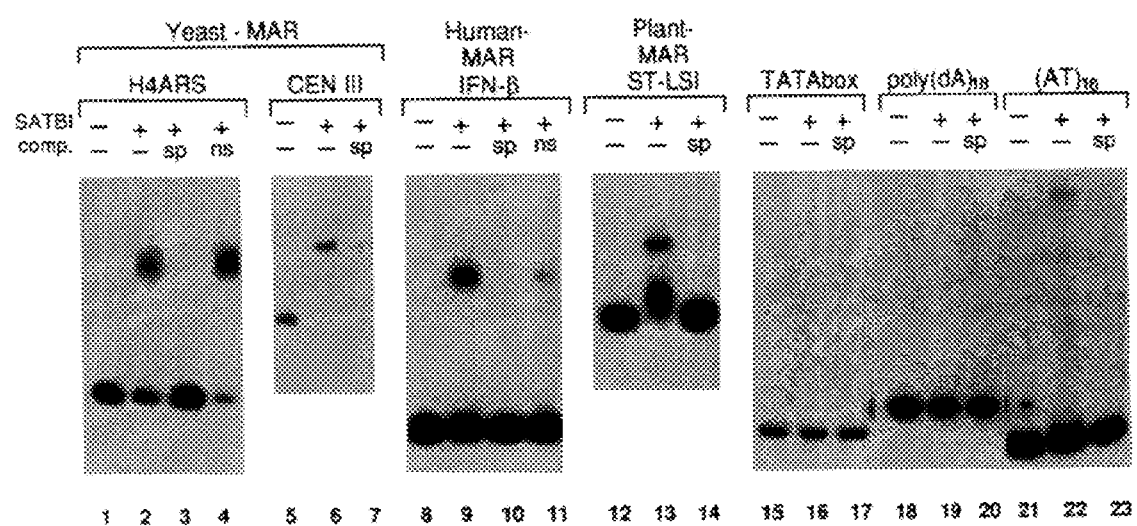
FIG. 8 shows the results of the mobility shift assay with MAR and Non-MAR DNA Probes. SATB1 synthesized in reticulocyte lysate was used in gel-mobility shift assays with the probes indicated above the lanes. Lanes indicated by (–) contain samples with no protein (SATB1) or competitor (comp.) added to the binding reaction; lanes marked by (+) contain samples to which protein was added. A 200-fold molar excess of specific competitor (sp) was present in the samples shown in lanes 3, 7, 10, 14, 17, 20 and 23, and non-specific competitor (ns) was added to the samples in lanes 4 and 11. The non-specific competitor was a 445 bp PvuII restriction fragment isolated from Bluescript.

To determine whether SATB1 is indeed a MAR-binding protein and capable of binding to MARs from different species, as does the MAR binding protein ARBP, purified from chicken oviduct, mobility shift assays were conducted. FIG. 8 shows an autoradiogram of gel mobility shift experiments carried out with yeast histone H4ARS as described in Umek and Kowalski, *Cell* 52:559–567 (1988) and yeast centromere CENIII probes (Fitzgerald-Hayes et al., supra) (lanes 1–7), which have previously been shown to attach to the nuclear scaffold, a MAR fragment from the human interferon-b (IFN-β) gene (Klehr et al, supra) (lanes 8–11), and a MAR from the potato ST-LSI gene (Stockhaus et al., supra) (lanes 12–14). In each case, addition of SATB1 to the binding reaction resulted in the appearance of a shifted band (lanes 2, 6, 9, and 13), which was inhibited by specific, unlabeled competitor DNA (lanes 3, 7, 10 and 14) but not by a Bluescript fragment as a non-specific competitor (shown only in lanes 4 and 11). In addition, the yeast centromere CEN II as well as MARs from the human β-globin gene described in Jarman and Higgs, *EMBO J.* 7:3337–3344 (1988) and the Drosophila 87A7 heat shock gene described in Mirkovitch et al., *Cell* 39:223–232 (1984) showed equally strong binding to SATB1. A synthetic poly $(dA-dT)_{16}$ repeat was found to be complexed weakly by the protein (lanes 21–23), which is consistent with the fact that poly(dA–dT) repeats are present in the MAR sequence of the human β-globin gene. When the wild type $(25)_7$ probe was used as a competitor, SATB1 binding to MARs was inhibited showing that there exist common SATB1 recognition site(s) in the two types of DNA.

Other types of AT-rich sequences were tested, which are not MARs and which do not unwind, for SATB1 binding (FIG. 8). SATB1 did not bind to DNA fragments containing a TATA box of the sequence TATAAT, or a poly$(dA)_{18}$·poly$(dT)_{18}$ tract (lanes 15–20). Furthermore, the AT-rich spacer region from Xenopus oocyte 5S DNA (Fedoroff and Brown, supra) was not a target for binding, even though it is 95% AT-rich and consists mostly of $A_4T_4$ repeats. The oligonucleotides 33 bp-poly(dG–dA) and 31 bp-poly(dA–dC), as well as an Oxytricha telomere sequence ($A_4C_4$) also did not have affinity to SATB1 as shown by gel-mobility shift assays. Thus, SATB1 distinguishes AT rich sequences that can, under superhelical strain, unwind from those that cannot unwind at the level of double-stranded DNA, in the absence of superhelical strain.

EXAMPLE XI

Tissue-Specific SATB1 Expression

Total cellular RNA was prepared from frozen mouse tissues or tissue culture cells by the guanidium thiocyanate method described in Chirgwin et al., *Biochem.* 18:5294–5299 (1979), incorporated herein by reference. Human RNA was purchased from Clontech. For Northern blots, total cellular RNA (10 µg/lane) was separated by formaldehyde agarose gel electrophoresis was as described (Maniatis, Supra). RNA was transferred to a Zetaprobe membrane in 10× SSC and fixed to the membrane by UV-crosslinking. Filters were prehybridized, hybridized to a radiolabeled probe and washed according to standard procedures described in Maniatis, supra.

RNase protection experiments were carried out as follows: the 5' BamHI(polylinker)-Bgl II(1278) fragment of pAT1146 was subcloned in the BamHI restriction site of Bluescript, linearized with NcoI(1082) and radiolabeled antisense RNA was synthesized with T7 RNA polymerase (Stratagene) as described by the manufacturer. The riboprobe was 244 bases (including 48 bases derived from Bluescript) in length and the size of the protected fragment was 196 bp. RNase probe protection was performed with 25 µg total cellular RNA as described in Melton et al., *Nucl. Acid Res.* 12:7035–7036 (1984), incorporated herein by reference, except that digestion was at 30° C. for 30 minutes with 50 µg/ml RNase A (Sigma) and 900 units/ml RNase T1 (BRL). RNA was precipitated in the presence of 20 µg glycogen/sample as a carrier. DNA probes for Northern hybridizations were labeled by random oligonucleotide priming (Pharmacia).

Figure 9A:
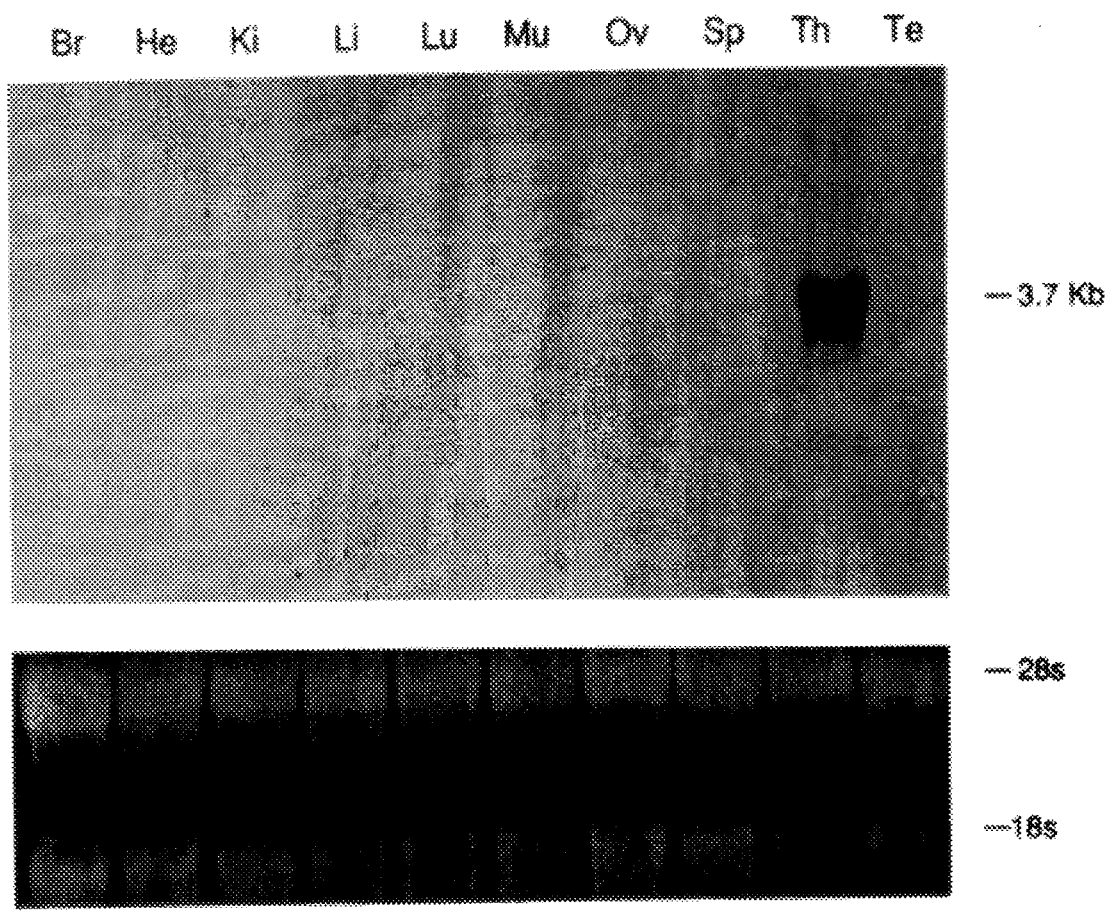
(FIG. 9A) Northern blot analysis. 10µ each of total cellular RNA from mouse tissues was analyzed using a radiolabeled AvaI(392)-BglII(1278) restriction fragment from pAT1146 (FIG. 1A) as a probe. The major transcript of 3.7 kb in thymus is marked. The same size transcript was also detected in human thymus RNA (data not shown). Abbreviations are: Br=brain, He=heart, Ki=kidney, Li=liver, Lu=lung, Mu=muscle, Ov=ovaries, Sp=spleen, Th=thymus, Te=testis. The bottom panel is a photograph of the ethidium bromide stained 28S and 18S rRNA bands on the formaldehyde gel before transfer to the hybridization membrane, to show that equal amounts of RNA were loaded in each track.

The nature of the SATB1 mRNA and its tissue distribution was examined by Northern and RNase protection experiments with total cellular RNA isolated from mouse and human tissues. The Northern blot shown in FIG. 9A was done with RNA from mouse tissues (5–8 weeks old) and a uniformly labeled restriction fragment (containing nucleotides 294 to 1278) derived from pAT1146 which lacked the sequence encoding the glutamine stretch (which is present in other genes) and the AT-rich, untranslated 5' region and was therefore expected to be very specific for SATB1 transcripts. A major transcript of 3.7 kb, and some minor bands, were detected in thymus (FIG. 9A). The size and the pattern of bands were identical between human and mouse thymus. Surprisingly, SATB1 mRNA was undetected in most other tissues, with the exception of brain which expressed a minute amount of SATB1 transcripts, visible only after overexposure of the films. No transcript was detected in testis RNA (even after long film exposure), although the SATB1 expressing cDNA was originally isolated from a testis library.

Figure 9B:
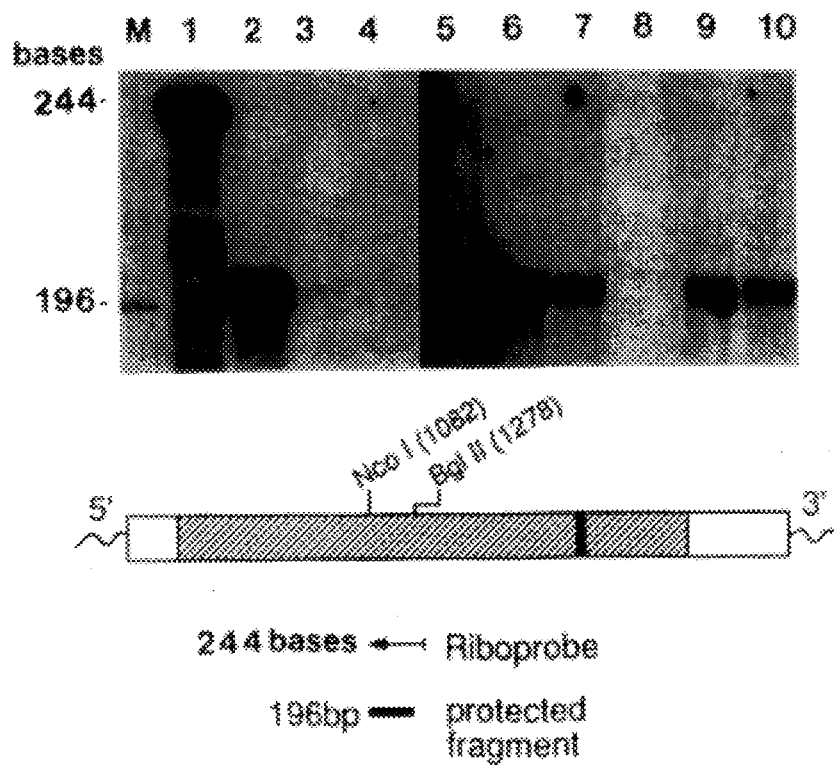
(FIG. 9B) Ribonuclease protection assay. The sizes of the undigested probe (244 bases) and of the RNase resistant fragments (196 bp) are indicated. The control lane (1) contains undigested probe. Total cellular RNA (25 µg each) was from human thymus (lanes 2 and 5), testis (lanes 3 and 6), and the human testicular cell-line Germa-1 (Hofmann et al., 1989a) (lanes 4 and 7). The panel on the right with lanes 5 and 7 is an overexposure of the autoradiograph shown on the left, to confirm the presence of a 196 bp protected RNA transcript in testis and Germa-1.

To determine whether SATB1 was expressed in a very small amount in testis, which would be below the limit of detection by Northern hybridization, RNA from human testis and thymus was analyzed by RNase protection. The autoradiogram in FIG. 9B reveals the presence of a small amount of SATB1 specific transcript in total cellular RNA from human testis (lane 3) and from a human testicular cell-line, Germa-1, described in Hofmann et al., *Cancer Res.* 49:4696–4700 (1989) (lane 4). An overexposure of the same gel is shown in the right panel to confirm the presence of the SATB1 specific band in testis (lane 6) and Germa-1 (lane 7). The amount of SATB1 specific transcript was substantially lower in testis (lanes 3, 6) than in thymus (lanes 2, 5). These results indicate that thymus is the major tissue of SATB1 expression, both in human and mouse, and the SATB1 encoding cDNA isolated from testis originated from a very rare RNA in this tissue.

Immunofluorescence data obtained with anti-SATB1 antiserum revealed that SATB1 is expressed in thymocytes. It was unexpected that the MAR-binding protein SATB1 exhibits tissue specificity, for it is generally believed that MAR-binding proteins would be structural components of the nuclear matrix and should be found in every tissue. This specific tissue distribution suggest that MAR-binding proteins could have specific roles other than the organization of chromatin structure.

EXAMPLE XII

Gel Electrophoresis and Western Blots

For Western blot analysis, whole cell extracts from mouse tissues were prepared by Dounce homogenizing tissue samples in 10 mM sodium phosphate pH 7.5, 0.5 mM DTT, 10% glycerol, 0.4 KCL, 100 µg/ml aprotinin and 34 µg/ml phenylmethanesulfonyl fluoride, followed by centrifugation (1 hour, 100,000× g). The cleared supernatants were incubated for 1 hour at room temperature with rabbit anti-SATB1 serum and the antigen-antibody complexes were precipitated with protein A-sepharose glass beads. The precipitate was washed three times with PBS containing 0.1% NP40, resuspended by boiling in SDS sample buffer and separated on SDS-PAGE (Laemmli, supra). The proteins separated on SDS-PAGE were electrophoretically transferred to Immobilon P membranes (Millipore) in 10 mM CAPS and 10% methanol as described in Matsudeira, *J. Biol. Chem.* 21:10035–10038 (1987), incorporated herein by reference. Antigenic protein was detected by incubating the blots with SATB1 antiserum in Tris/saline with 10% BSA, followed by several washes in Tris/saline and incubation with horseradish peroxidase-labeled goat anti-rabbit immunoglobulin (1:2000 dilution) and subsequent treatment of the blots with 5 mg/ml diaminobenzidine, 1% hydrogen peroxide. To confirm that pAT1146 contains the complete SATB1 coding sequence, rabbit anti-SATB1 antibodies were generated in order to compare the size of the bacterially produced SATB1 with the native protein isolated from mouse thymus.

EXAMPLE XIII

Preparation of Rabbit Anti-SATB1 Antibody

Thrombin cleaved 80 Kd-ΔSATB1 protein was used for immunizing rabbits. Rabbits were immunized subcutaneously with approximately 500 µg of protein as a 1:1 mixture with Freund's complete adjuvant. Subsequent immunizations were performed at 4-week intervals. Sera were obtained 10–14 days after each boost. The antiserum which exhibited 160,000 titer in a standard ELISA assay was used in this study with horseradish peroxidase-labeled goat anti-rabbit as the secondary antibody.

For synthesis of a glutathione-S-transferase (GST)-ΔSATB1 fusion protein the cDNA clone pAT1146 was cut with AvaI (392) downstream of the start codon and with XbaI(polylinker) at the 3' end, blunt-ended with Klenow and ligated in the blunt-ended EcoRI site of the expression vector pGEX-2T (Pharmacia). The plasmid with the correct orientation was selected. The synthesized, thrombin cleaved protein was therefore 80 Kd in size, because 59 amino acids of the N-terminal were missing. Protein synthesis, purification of the GST-ΔSATB1 fusion protein and removal of the GST portion by cleavage with thrombin was as described in Smith and Johnson, *Gene* 67:31–40 (1988) and Gearing et al., *Bio/Tech* 7:1157–1161 (1989), both of which are incorporated herein by reference. The resulting 80 Kd ΔSATB1 protein was used for gel shift assays where indicated and referred to as "bacterially produced SATB1" in the text. A mammalian expression plasmid that expresses SATB1 driven by the SV40 enhancer-promoter sequence was constructed using Bluescript that contains the BamHI-PvuII fragment of PECE (Ellis et al., *Cell* 45:721–732 (1986), recloned into the bluescript vector provided by Dr. C. Hauser). The BamHI-PvuII fragment was blunt-ended and recloned into the PvuII sites of Bluescript. To this vector, the whole pAT1146 was inserted at the EcoRI site.

Figure 9C:
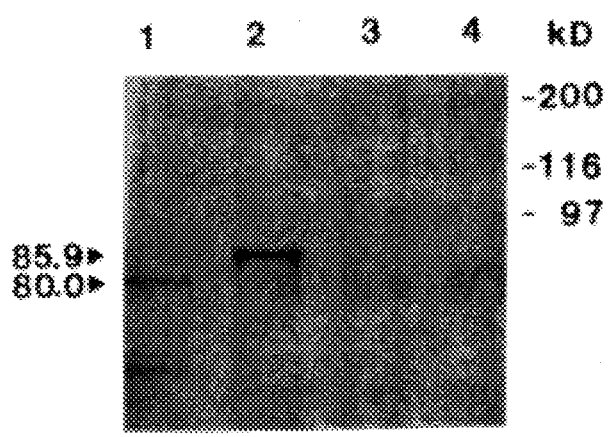
(FIG. 9C) Western blot with rabbit anti-SATB1 serum. Lane 1: bacterially produced, thrombin cleaved ΔSATB1, lane 2: whole cell extract from mouse thymus, containing 10 µg total protein, lane 3 and 4: whole cell extract from mouse liver, containing 10 µg and 20 µg total protein/lane, respectively. Size markers are shown on the right in kilodaltons. The predicted sizes of 85.9 Kd for the full-length SATB1 protein, and of 80.0 Kd for the truncated, thrombin cleaved GST-ΔSATB1 protein are indicated on the left. Western blot analysis using thymus and liver cell extract without immunoprecipitation revealed a specific band in thymus, but not in liver.

Cell extracts from thymus, liver and thrombin cleaved GST-ΔSATB1 fusion protein were subjected to immunoprecipitation with anti-SATB1 antibody. The immunoprecipitates were separated on SDS-PAGE and identified by Western blotting with anti-SATB1 rabbit serum. A prominent band of about 85 Kd is visible in the thymus extract (FIG. 9C, lane 2) which is in perfect agreement with the 85.9 Kd size predicted by the cDNA pAT1146. No band was detected in liver extract (lanes 3 and 4). Bacterially produced SATB1 was slightly smaller (lane 1), because 59 amino-terminal amino acids were deleted from pAT1146 prior to cloning it into the expression vector pGEX-2T thereby reducing the size of the protein to 80.0 Kd.

These results are in agreement with the proposal that the cDNA clone pAT1146 encodes a full-length SATB1 protein, even though the size of the cDNA (2.9 kb) is smaller than the mRNA size (3.7 kb).

EXAMPLE XIV

Cellular Localization of SATB1

To study the cellular localization of SATB1, indirect immunofluorescence analysis was used. Mouse Ltk⁻ cells were transfected with a mammalian expression plasmid PECESATB1 and plated on slides. Two days after transfection, the cells were fixed with methanol and blocked with 100-fold PBS dilution of normal goat serum, followed by treatment with 20-fold dilution of rabbit anti-SATB1 serum and 20-fold diluted FITC-conjugated goat-anti-rabbit serum containing Hoechst 32258.

The cellular localization of SATB1 in mouse Ltk cells was examined after transiently transfecting a mammalian expression construct that expresses the SATB1 gene. This system was chosen for study instead of thymocytes because nuclei are more easily distinguished from cytoplasm in mouse Ltk– cells. The transfected cells were allowed to grow on a glass slide for two days and SATB1 was detected by indirect immunofluorescence analysis using FITC conjugated goat anti-rabbit serum. The chromosomes on the same slide were stained with Hoechst 33258 described in Weinsblum and Haenssler, *Chromosoma* 46:255 (1974) and Hilwig and Gropp, *Exp. Cell Res.* 75:122–126 (1972).

SATB1 is localized in the nuclei of transfected Ltk– cells. In interphase nuclei, the SATB1 fluorescent signals are found throughout the nuclei, but do not appear diffuse. In the telophase nuclei, the SATB1 fluorescence signals are found at the nuclear periphery, instead. This could be of interest since the nuclear membranes that break down into small vesicles at prometaphase reassemble around each group of chromosomes at telophase to form the two daughter interphase nuclei. Although SATB1 is a nuclear protein, no apparent sequence that corresponds to the nuclear localization signal was found.

EXAMPLE XV

SATB1 Localization in the Nuclear Matrix Fraction of Thymocytes

To determine whether SATB1 is a component in nuclear matrix, nuclear matrix or scaffold was prepared according to Mirkovitch et al., *Cell* 39:223–232 (1984) with some modification as described in Mielke et al., supra. Briefly, thymocytes were prepared from thymus of 3-week old mice and nuclei were isolated by mixing the cells in reticulocyte suspension buffer (100 mM NaCl, 10 mM MgCl$_2$, 10 mM TrisHCl, pH 7.4) containing 0.5% NP-40 followed by centrifugation at 700 g for 10 minutes. Nuclei (2×10$^8$) were washed twice with the same buffer before extracted with 8 ml of LIS medium (15 mM lithium 3,5-diiodosalicylate, 20 mM N-(2-hydroxyethyl)piperazine-N'-2-ethanesulfonic acid (HEPES)-NaOH, pH 7.4, 0.1M lithium acetate, 1 mM EDTA, 0.1% digitonin) to remove histones and other nuclear proteins. The precise method for extraction of nuclei and purification of nuclear matrix is described in Mielke et al., supra.

The resulting insoluble nuclear matrix (nuclear halos) was transferred to 40 ml of digesting buffer (20 mM TrisHCl, pH 7.4, 0.05 mM spermine, 0.125 mM spermidine, 20 mM KCl, 70 mM NaCl, 10 mM MgCl$_2$) and were gently rocked in a capped tube for 30 minutes and centrifuged as before. After repeating this process three times, the nuclear halos were digested with 100 mg each of DNase I and RNase A (Boehringer Mannheim) in 1 ml of digesting buffer for 30 minutes at room temperature and centrifuged at 10,000 rpm for 10 minutes. The precipitate (nuclear matrix fraction) was either directly suspended in Laemmli sample buffer (Laemmli, supra) or extracted according to Miller et al., *Cancer Res.* 52:422–427 (1992), incorporated herein by reference, and precipitated with 70% acetone followed by centrifugation at 13,000 g for 20 minutes before being suspended in sample buffer. The supernatant from the LIS extraction was precipitated with a final concentration of 2M NaCl and the precipitate was washed with 70% acetone, 20% ethanol, 10 mM TrisHCl (pH 7.4) as described in Hofmann et al., *Cell* 57:725–737 (1989), incorporated herein reference. The pellet was treated with DNase I and RNase A as described above and the proteins were precipitated with 70% acetone at 13,000 g for 20 minutes and suspended in sample buffer.

SATB1 binds MARs and is found in nuclei. The next obvious question is whether SATB1 is a component of the nuclear matrix. Nuclear matrix preparation was by the lithium diiodosalicylate (LIS) extraction method according to Mirkovitch et al., supra, using thymocytes isolated from 3 week old mice thymus. Western blot analysis of the proteins in the nuclear matrix fraction with the rabbit anti-SATB1 antibody revealed that SATB1 is present in the nuclear matrix fraction of thymocytes.

EXAMPLE XVI

SATB1 Does Not Bind Single Stranded DNA

End-labeled, double-stranded [wt(25)$_7$] was denatured by boiling for 5 minutes and quick cooling on ice. This denatured probe was then incubated with bacterially produced SATB1 and protein-binding was analyzed by typical gel-mobility shift assay. Under these conditions, SATB1 did not bind to the denatured probe, but bound with high affinity to the double stranded probe.

EXAMPLE XVII

Transfection of Vectors Containing AT1146 DNA

The effect of SATB1 overexpression was studied in Ltk− cells, NIH3T3 cells and HeLa cells in which endogenous SATB1 is absent. SATB1 expression constructs were cotransfected into the various cell lines using the calcium phosphate procedure as described in Maniatis et al., §§16.30–16.47, supra, and selected for neomycin resistant cell clones. Single colonies were initially detected for Ltk− and NIH3T3 cells, but after proliferating to approximately 100 cells, they abruptly died showing cell fragmentation. The fast dividing HeLa cell transformants did not yield single colonies resistant to neomycin. The control expression plasmid without the SATB1 gene gave rise to many healthy clones that continued to proliferate under the neomycin selection. A possible explanation for this phenomena may be that SATB1 suppressed the neomycin resistant gene. However, the morphology of cells resembled that of cells undergoing apoptosis. Without neomycin selection, a significant decrease in cell number after transient transfection with the PECESATB1 expression plasmid was detected in comparison with cells transfected with control PECE plasmid, which was observed only when a high efficiency transfection was achieved. It is possible that high levels of SATB1 induce cell death through apoptosis.

EXAMPLE XVIII

Transcriptional Suppression by SATB1

Figure 10:
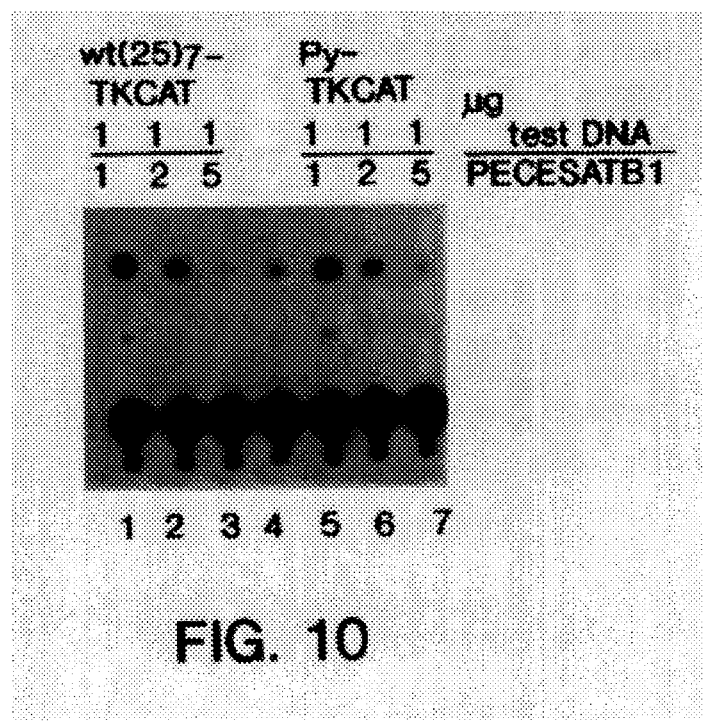
FIG. 10 show the results of the SATB1 transcriptional suppression assay by SATB1.

A transient cotransfection assay was conducted using the DEAE/Dextran procedure as described in Maniatis et al., supra. One μg of either wild-type $(25)_7$ TKCAT [wt$(25)_7$ TKCAT] (lanes 1–3) or polyoma enhancer TKCAT [PyTKCAT] (lanes 5–7) and the indicated amount (1, 2 or 5 μg) of mammalian SATB1 expression plasmid, PECESATB1, containing SV40 enhancer/promoter according to current conventional methods. Two days later, cell extracts were obtained and CAT activity was measured using gel electrophoresis. Lane 4 represents CAT activity for cells transfected with TKCAT only. (See FIG. 10).

Although the invention has been described with reference to the disclosed embodiments, it should be understood that various modifications can be made without departing from the spirit of the invention. Accordingly, the invention is limited only by the following claims.

We claim:

1. A purified human SATB1 protein that binds a matrix/scaffold-associating DNA region (MAR), said protein having a deduced molecular weight of about 85.9 kD, said MAR comprising at least two ATC sequences, said ATC sequence comprising a double-stranded nucleic acid sequence of about ten to about forty nucleotides that is greater than about 66% AT-rich, said nucleic acid sequence further comprising in one strand, in addition to adenine and thymine residues, either only cytosine residues or only guanine residues, wherein said ATC sequences unwind when subjected to superhelical stress.

2. The purified protein of claim 1, said protein comprising the amino acid sequence of SEQ. ID. NO. 2.

* * * * *

UNITED STATES PATENT AND TRADEMARK OFFICE
CERTIFICATE OF CORRECTION

PATENT NO.    : 5,652,340
DATED         : July 29, 1997
INVENTOR(S)   : Kohwi-Shigematsu et al.

It is certified that error appears in the above-identified patent and that said Letters Patent is hereby corrected as shown below:

Title page, Item [54], column 1, line 1,
Item [54], please delete ", NUCLEIC ACIDS ENCODING THE SAME AND METHODS FOR DETECTING THE NUCLEIC ACIDS"

Column 9,
Line 12, please delete "Anchoring" and replace therefor with -- anchoring --

Table 1,
Line 14, (amino acid position 134) please delete the "Y" and replace therefor with -- V --.
Please delete all the "O" and replace therefor with -- Q --.
Line 16, (amino acid position 163) please delete "A".

Column 17,
Line 67, please delete "round" and replace therefor with -- rounds --.

Column 19, Table 3,
Please delete "3'" and replace therefor with -- 5' --.
Please delete "5'" and replace therefor with -- 3' --.

Column 22,
Line 6, please delete "4" and replace therefor with -- 14 --.

Column 24,
Line 29, please delete "NaC1 TE" and replace therefor with -- NaC1/TE --.

UNITED STATES PATENT AND TRADEMARK OFFICE
CERTIFICATE OF CORRECTION

PATENT NO.    : 5,652,340
DATED         : July 29, 1997
INVENTOR(S)   : Kohwi-Shigematsu et al.

It is certified that error appears in the above-identified patent and that said Letters Patent is hereby corrected as shown below:

Column 25,
Line 57, please delete "indicting" and replace therefor with -- indicating --.

Signed and Sealed this

Twenty-fifth Day of December, 2001

Attest:

JAMES E. ROGAN
*Director of the United States Patent and Trademark Office*

*Attesting Officer*